(12) United States Patent
Rypacek et al.

(10) Patent No.: US 7,160,592 B2
(45) Date of Patent: Jan. 9, 2007

(54) POLYMER COATING FOR MEDICAL DEVICES

(75) Inventors: Frantisek Rypacek, Prague (CZ);
Monika Lapcikova, Prague (CZ);
Ludka Machova, Prague (CZ)

(73) Assignee: CV Therapeutics, Inc., Palo Alto, CA (US)

(*) Notice: Subject to any disclaimer, the term of this patent is extended or adjusted under 35 U.S.C. 154(b) by 0 days.

(21) Appl. No.: 10/366,767

(22) Filed: Feb. 14, 2003

(65) Prior Publication Data

US 2003/0219562 A1    Nov. 27, 2003

Related U.S. Application Data

(60) Provisional application No. 60/357,573, filed on Feb. 15, 2002.

(51) Int. Cl.
| B32B 1/08 | (2006.01) |
| B32B 27/36 | (2006.01) |
| B32B 15/08 | (2006.01) |
| B32B 15/09 | (2006.01) |
| B32B 27/06 | (2006.01) |
| A61F 2/00 | (2006.01) |
| A61F 2/06 | (2006.01) |
| A61F 2/82 | (2006.01) |
| B29D 23/00 | (2006.01) |

(52) U.S. Cl. .................. 428/36.9; 428/36.91; 428/447; 428/450; 428/480; 424/422; 623/1.38; 623/1.42; 623/1.44; 623/1.46; 604/890.1; 604/891.1

(58) Field of Classification Search ............ 428/36.91, 428/447, 448, 450, 480, 36.9; 424/422–426; 623/1.38, 1.42, 1.43, 1.44, 1.46; 604/890.1, 604/891.1
See application file for complete search history.

(56) References Cited

U.S. PATENT DOCUMENTS

| 4,104,296 | A | * | 8/1978 | Pike |
| 4,215,165 | A | * | 7/1980 | Gras et al. |
| 4,268,554 | A | * | 5/1981 | Gras |
| 4,591,652 | A | * | 5/1986 | DePasquale et al. |
| 4,733,665 | A |   | 3/1988 | Palmaz .................. 606/108 |
| 4,800,882 | A |   | 1/1989 | Gianturco ............... 606/194 |
| 4,886,062 | A |   | 12/1989 | Wiktor ................... 606/194 |
| 4,916,193 | A |   | 4/1990 | Tang et al. .............. 525/413 |
| 4,994,071 | A |   | 2/1991 | MacGregor ............. 606/194 |
| 5,019,096 | A | * | 5/1991 | Fox, Jr. et al. |
| 5,053,048 | A |   | 10/1991 | Pinchuk .................. 623/1.43 |

(Continued)

FOREIGN PATENT DOCUMENTS

EP    0484057    10/1991

(Continued)

OTHER PUBLICATIONS

Lofgren, A., et al., Recent Advances in Ring-Opening Polymerization of Lactones and Related Compounds, *J.M.S. Rev. Macromol. Chem. Phys*, C35:379-418 (1995).

(Continued)

*Primary Examiner*—Jennifer C. McNeil
*Assistant Examiner*—Chris Bruenjes
(74) *Attorney, Agent, or Firm*—CV Therapeutics, Inc.

(57) ABSTRACT

Coatings are provided in which surfaces may be activated by covalently bonding a silane derivative to the metal surface, covalently bonding a lactone polymer to the silane derivative by in situ ring opening polymerization, and depositing at least one layer of a polyester on the bonded lactone. Biologically active agents may be deposited with the polyester layers. Such coated surfaces may be useful in medical devices, in particular stents.

51 Claims, 8 Drawing Sheets

U.S. PATENT DOCUMENTS

| | | | |
|---|---|---|---|
| 5,100,991 A * | 3/1992 | Cray et al. | |
| 5,221,698 A | 6/1993 | Amidon et al. | 523/122 |
| 5,304,121 A | 4/1994 | Sahatjian | 604/509 |
| 5,464,650 A | 11/1995 | Berg | 427/2.3 |
| 5,527,337 A | 6/1996 | Stack et al. | 606/198 |
| 5,545,208 A | 8/1996 | Wolff et al. | 623/1.22 |
| 5,643,681 A | 7/1997 | Voorhees et al. | 428/483 |
| 5,649,977 A | 7/1997 | Campbell | 623/1.15 |
| 5,679,400 A | 10/1997 | Tuch | 427/2.14 |
| 5,686,546 A * | 11/1997 | Henderson | |
| 5,786,022 A | 7/1998 | Agarwal et al. | 427/2.31 |
| 5,820,917 A | 10/1998 | Tuch | 427/2.1 |
| 5,866,702 A | 2/1999 | Mackman et al. | 544/277 |
| 5,980,551 A | 11/1999 | Summers et al. | 606/194 |
| 5,997,954 A * | 12/1999 | Decker et al. | |
| 6,013,855 A | 1/2000 | McPherson et al. | 623/23.76 |
| 6,103,848 A * | 8/2000 | Decker et al. | |
| 6,120,847 A | 9/2000 | Yang et al. | 427/335 |
| 6,180,615 B1 | 1/2001 | Zablocki et al. | 514/46 |
| 6,214,807 B1 | 4/2001 | Zablocki et al. | 514/46 |
| 6,231,590 B1 | 5/2001 | Slaikeu et al. | |
| 6,248,127 B1 | 6/2001 | Shah et al. | 623/1.15 |
| 6,265,016 B1 | 7/2001 | Hostettler et al. | 427/2.11 |
| 6,313,254 B1 * | 11/2001 | Meijs et al. | |
| 6,335,029 B1 * | 1/2002 | Kamath et al. | 424/423 |
| 6,335,340 B1 | 1/2002 | Gallagher et al. | 514/252.05 |
| 6,342,591 B1 * | 1/2002 | Zamoria et al. | |
| 6,344,496 B1 * | 2/2002 | Niederauer et al. | |
| 6,361,819 B1 * | 3/2002 | Tedeschi et al. | |
| 6,521,431 B1 * | 2/2003 | Kiser et al. | |
| 6,627,724 B1 * | 9/2003 | Meijs et al. | |
| 6,641,611 B1 * | 11/2003 | Jayaraman | 623/1.42 |
| 2003/0077310 A1 * | 4/2003 | Pathak et al. | 424/423 |
| 2003/0087922 A1 * | 5/2003 | Bethiel et al. | 514/275 |
| 2003/0099712 A1 * | 5/2003 | Jayaraman | 424/486 |

FOREIGN PATENT DOCUMENTS

| | | |
|---|---|---|
| EP | 0716836 | 12/1995 |
| EP | 0982041 | 8/1999 |
| WO | 9000343 | 1/1990 |
| WO | 9805335 | 2/1998 |
| WO | 9902168 | 1/1999 |
| WO | 9908729 | 2/1999 |
| WO | 9930684 | 6/1999 |
| WO | 9955396 | 11/1999 |
| WO | 0044750 | 8/2000 |
| WO | 0078776 | 12/2000 |
| WO | 0078779 | 12/2000 |

OTHER PUBLICATIONS

Brinker, C.J., Scherer, G.W., Sol-Gel Science: the Physics and Chemistry of Sol-Gel Processing, *Academic Press*, New York, pp. 130-139 (1990).

Jang, J., Kim, E.K., Corrosion Protection of Epoxy-Coated Steel Using Different Silane Coupling Agents, J. *Applied Polym. Sci*, 71:585-593 (1999).

Dubois, P., et al., Aluminium Alkoxides: A Family of Versatile Initiators for the Ring-Opening Polymerization of Lactones and Lactides, *Makromol. Chem., Macromol. Symp.*, 42/43: 103-116 (1991).

Jonte, J.M., et al., Polylactones 4. Cationic Polymerization of Lactones *by Means of Alkysulfonates, J. Macromol. Sci. Chem.*, A23:495-514 (1986).

Kricheldorf, H.R., et al., Anionic and Pseudoanionic Polymerization of Lactones- a Comparison, *Makromol. Chem., Macromol. Symp.*, 32:285-298 (1990).

Kricheldorf, H.R., et al., Poly(lactones). 9. Polymerization Mechanism of Metal Alkoxide Initiated Polymerizations of Lactide and Various Lactones, *Macromolecules*, 21:286-293 (1988).

Higuchi, T., Rate of release of medicaments from ointment bases containing drugs in suspensions, *J. Pharm. Sci.*, 50:874-875 (1961).

Higuchi, T., Mechanism of sustained-action medication, theoretical analysis of rate of release of solid drugs dispersed in solid matrices, *J.Pharm.Sci.*, 52:1145-1149 (1963).

* cited by examiner

POLYMER COATING FOR MEDICAL DEVICES

CROSS-REFERENCE TO RELATED APPLICATION

This application claims benefit to U.S. Provisional Application No. 60/357,573 filed Feb. 15, 2002.

BACKGROUND OF THE INVENTION

1. Field of the Invention

The invention relates to a polymer coated metal surface in which at least one polymer layer is covalently bonded to the activated metal surface. The polymer coating may contain one or more biologically active agents. The polymer coated metal can be used in an implantable medical device such as a stent. The invention further relates to methods of coating metals surfaces and preparing medical devices.

2. Description of the Related Art

Many surgical interventions require the placement of a medical device into the body. While necessary and beneficial for treating a variety of medical conditions, the placement of metal or polymeric devices in the body can give rise to numerous complications. Some of these complications include increased risk of infection, initiation of a foreign body response resulting in inflammation and fibrous encapsulation, and/or initiation of a wound healing response resulting in hyperplasia and/or restenosis. These and other possible complications must be dealt with when introducing a metal or polymeric device into the body.

One approach to reducing the potential harmful effects of such an introduction has been to attempt to improve the biocompatibility of the device. While there are several methods available to improve the biocompatibility of devices, one method which has met with limited success is to provide the device with the ability to deliver biologically active agents to the vicinity of the implant. By so doing, some of the harmful effects that can be associated with the implantation of medical devices can be diminished. For example, antibiotics can be released from the device to minimize the possibility of infection, and anti-proliferative drugs can be released to inhibit hyperplasia. Another benefit to the local release of biologically active agents is the avoidance of toxic concentrations of drugs which are sometimes necessary when given systemically to achieve therapeutic concentrations at the site where they are needed.

Those skilled in the art of medical devices have been challenged to meet the several stringent criteria for implantable medical devices. Some of these challenges are: 1) the requirement, in some instances, for long term (days, weeks, or months) release of biologically active agents; 2) the need for a biocompatible, non-inflammatory surface on the device; 3) the need for significant durability, particularly with devices that undergo flexion and/or expansion when being implanted or used in the body; 4) concerns regarding processability, to enable the device to be manufactured in an economically viable and reproducible manner; and 5) the requirement that the finished device be capable of being sterilized using conventional methods.

Several implantable medical devices capable of delivering medicinal agents have been described. Several patents are directed to devices utilizing biodegradable or bioresorbable polymers as drug containing and releasing coatings, including Tang et al, U.S. Pat. No. 4,916,193 and MacGregor, U.S. Pat. No. 4,994,071. Other patents are directed to the formation of a drug containing hydrogel on the surface of an implantable medical device, these include Amiden et al, U.S. Pat. No. 5,221,698 and Sahatijian, U.S. Pat. No. 5,304,121. Still other patents describe methods for preparing coated intravascular stents via application of polymer solutions containing dispersed therapeutic material to the stent surface followed by evaporation of the solvent. This method is described in Berg et al, U.S. Pat. No. 5,464,650.

A number of approaches have been used to try to overcome the challenges listed above. The below are examples of these approaches.

McPherson, et. al., U.S. Pat. No. 6,013,855, describes methods for grafting hydrophilic polymers onto metal surfaces. This method included exposing the device surface to a silane coupling agent and causing the agent to be covalently bound to the device surface. The bonded silane layer was then exposed to a hydrophilic polymer such that the hydrophilic polymer became covalently bound to the silane layer.

Pinchuck, U.S. Pat. No. 5,053,048, describes curing a silane compound or compounds onto a surface to form a hydrophilic matrix. An antithrombogenic agent was then coupled to the amine group on the aminosilane three-dimensional matrix to provide a thromboresistant coating to the surface.

Lee, et. al., U.S. Pat. No. 6,335,340, describes methods for coating oxide surfaces and coatings that rendered such surfaces hydrophilic. A functional group (Z) such as $SiCl_3$ was associated with the surface. A tether of a hydrophobic covalent attachment, typically of approximately 5 to 20 bonds in length, was formed with Z. A biopolymer-resistant domain was then adhered to the tether to form the hydrophilic surface.

Hostettler, et. al., U.S. Pat. No. 6,265,016, describes chemically treating metal surfaces to affix amine-containing groups. A "tie coat" of a hydrophilic polyurethane was then covalently attached to the amine groups to form a slippery, hydrophilic polyurethane hydrogel.

Kamath, et. al., U.S. Pat. No. 6,335,029, describes applying at least one composite layer of a biologically active agent and a polymer to a base material by physical or covalent methods. At least one barrier layer was positioned over and applied to the composite layer by a low energy plasma polymerization process.

Shah, et. al., U.S. Pat. No. 6,248,127, describes coatings for medical devices in which a silane coating is adhered on the surface of the substrate and a film containing a heparin-biopolymer complex is created on the surface by covalent linkages.

However, there remain significant problems to overcome in order to provide a durable implantable medical device capable of delivering a therapeutically effective amount of a biologically active agent for an extended period of time. This is particularly true when the coating composition must be kept on the device in the course of flexion and/or expansion of the device during implantation or use. It is desirable to have a facile and easily processable method of controlling the rate of biologically active agent release from the surface of the device.

Although a variety of polymers have previously been described for use as drug release coatings, only a small number possess the physical characteristics that would render them useful for implantable medical devices which undergo flexion and/or expansion upon implantation. Many polymers which demonstrate good drug release characteristics, when used alone as drug delivery vehicles, provide coatings that are too brittle to be used on devices which undergo flexion and/or expansion. Other polymers can provide an inflammatory response when implanted. These or other polymers demonstrate good drug release characteristics for one drug but very poor characteristics for another.

In many respects, the success of a polymer coating depends on the nature of the contact between at least the polymer layer adjacent to the metal surface and the underlying metal surface. In particular, if the polymer cracks or peels away from the metal surface, the polymer and any biologically active agent contained therein may decrease in performance. If the polymer layer is designed to contain a biologically active agent to be released, the resulting polymer/biologically active agent composite may be prone to dilation, swelling, degradation, and/or volume changes because of interactions of the incorporated compound with aqueous environments of the body. Also, following the penetration of water into the polymer layer, dissolution of the compound and its subsequent release, may change the structure and porosity of the composite. In addition, due to penetration of water following drug dissolution, the polymer layer could be exposed to a mechanical stress due to osmotic forces. These effects may result in detachment of the polymer layer and its peeling from the metal surface. Further, the changes in the geometry of the polymer layer and the available surface area are potential sources of unpredictability of the release rate for the incorporated compounds. Due to a combination of these factors, the performance of the system decreases.

Accordingly, there is a persistent need for an improved polymer coating of metallic implants that provides a stable, biocompatible and low-profile polymer coating that, at the same time, provides a long-term release of biologically active agents for periods extending to weeks or months. Thus, there is a need for a method for securing the highly reproducible deposition of the polymer coating layer on the article surface. In many instances the polymer layer has to be thin enough so that it does not restrict the flexibility and adaptation of the metal device. Also, the polymer layer must resist damage due to device handling or deformation.

SUMMARY OF THE INVENTION

The invention provides for a coating for a metal surface with a metal-activating layer of polymerized silane derivatives covalently bound to the metal surface. A binding layer of one or more lactone polymers is covalently bonded to the polymerized silane derivative. The surface may further include a container layer of one or more sublayers of a polymer adhered to the binding layer.

In one embodiment of the invention, the composition of the binding layer or the container layer, or both, includes one or more biologically active agents. The biologically active agent(s) is about 0 to about 60 percent by weight of the binding or container layers. The biologically active agent is released from the composition in an aqueous environment.

In another embodiment of the invention, the metal-activating layer is a siloxane polymer having one or both of hydroxy- or amino-groups on the siloxane. The siloxane polymer is acylated by the polyester of the binding layer.

The binding layer and the container layers have at least one layer of one or more lactone polymers.

In the binding layer, the lactone polymer may be a lactone homopolymer such as polyglycolide, poly(L-lactide), poly(D-lactide), poly(C-caprolactone), poly(p-dioxanone), poly(dioxepanone), or a lactone copolymer such as poly(L-lactide-co-D-Lactide), poly(L-lactide-co-glycolide), poly(D-lactide-co-glycolide), poly(D,L-lactide-co-glycolide), poly(lactide-co-caprolactone), poly(lactide-co-dioxanone), poly(D,L-lactide), or poly(lactide-co-dioxepanone).

In the container layer, the polyester polymer may be either a lactone homopolymer, a statistical copolymer, or a block copolymer with at least one polylactone block, while the other block or blocks of the copolymer may be a polyether, a poly(amino acid), a poly(acrylate), a poly(methacrylate), or polybutadiene. In a preferred embodiment of the invention, the polymer of the container layer has a molecular weight of $10^3$ to $10^6$.

In various preferred embodiments, the binding layer is a polylactide and the container layer is one or more polymers such as poly(L-lactide), poly(glycolide), poly(lactide-co-glycolide) or poly(L-lactide-co-D-lactide), and the mole fraction of L-lactide structural units is in the range of either 0.7 to 1.0 or 0 to 0.3. The biologically active agent is about 0.5 to 60 percent of the total mass of polymer of the container layer.

In other preferred embodiments of the invention, the binding layer is a polylactide and the container layer is a polymer selected of poly(D,L-lactide) or poly(L-lactide-co-D-lactide) and the mole fraction of L-lactide structural units is in the range of 0.3 to 0.7. The biologically active agent is 0.5 to 60 percent of the total mass of container layer.

In still another embodiment of the invention, the container layer has two or more sublayers of the same or different polymers. The concentration of the biologically active agent(s) in an inner container sublayer may be different than the concentration of the biologically active agent(s) in an outer container sublayer.

In another preferred embodiment of the invention, the composition of the inner container sublayer is a semicrystalline polymer, or a semicrystalline mixture of polymers, and the outer container sublayer comprises at least one amorphous polymer. The polymer of an inner container sublayer may be a hydrophobic polymer which is either a lactone homopolymer, a statistical lactone copolymer, a lactone block copolymer, and the polymer of an outer container sublayer is an amphiphilic copolymer of at least one of a statistical copolymer and a block copolymer of lactones and ethylene oxide.

Yet another embodiment of the invention includes a method of coating a metal surface. The method includes reacting the metal surface with a silane-based activating reagent to form a metal surface having an activated layer, polymerizing at least one lactone via ring opening polymerization in the presence of the activating layer to form a metal surface having a binding layer, and depositing at least one solvent solution comprising a polymer on the binding layer and evaporating the solvent to form at least one container layer adhered to the binding layer. The silane-based activating reagent is a silane derivative of general formula $(R^2)_3$—$SiR^1$ wherein $R^1$ is independently selected from substituted alkyl, substituted alkenyl, substituted alkynyl, substituted aralkyl, substituted heteroaryl, and substituted alkoxy, with the proviso that $R^1$ contains a hydroxy or amino group, or a functional group that can be transformed to a radical that contains a hydroxy or amino group; wherein $R^2$ is independently selected from halo, optionally substituted alkoxy, optionally substituted aryloxy, optionally substituted silyloxy, or optionally substituted alkyl, with the proviso that all three $R^2$ substituents are not simultaneously substituted alkyl.

In a preferred embodiment, the silane-based activating reagent is an organo-trialkoxysilane derivative of a general formula R'—Si—$(OR)_3$ where R is a $C_{1-4}$ alkyl group, and R' is a hydroxyalkyl, aminoalkyl, or a functional group that can be transformed to hydroxyalkyl or aminoalkyl through a modification reaction.

In another preferred embodiment the silane-based activating agent is applied in a solution or in a vapor phase to form a metal activating layer bound to the metal surface. Formation of a binding layer by lactone polymerization includes immersing an activated metal surface in a lactone solution, or a lactone melt at a temperature sufficient to keep the lactone in the molten state, while both environments also contain a polymerization catalyst, for a time sufficient to allow the in-situ ring opening polymerization of the lactone on the activated layer to form the binding layer. Formation of a container layer includes the deposition of a solvent solution containing the polymer onto the binding layer by bringing a metal surface having the activation layer and binding layer into contact with a polymer solution by dipping the surface into the solvent solution or spraying, casting, pouring or spreading the solution onto the surface, and evaporating the excess solvent. The solvent solution may contain one or more biologically active compounds. In certain embodiments, the solvent is an aprotic solvent such as an ether, ketone, aromatic hydrocarbon and a mixture of these solvents. The catalyst may be a low-toxicity catalyst suitable for ring-opening polymerization of lactones by a coordination-insertion mechanism. The catalyst includes tin(II), zinc, calcium carboxylates, iron carboxylates, and alkyl aluminum compounds.

In still another embodiment of the invention, the polymer of the container layer is compatible with the polymer of the the binding layer. The container layer may be formed by deposition of one or more successive sublayers of polymer over the binding layer. Each sublayer of polymer may have the same composition as the previous container sublayer or each sublayer may vary in polymer composition. Each of these successive layers of polymer may contain one or more biologically active agents.

In yet another embodiment, the invention provides for a medical device having a metal surface with a metal-activating layer of polymerized silane derivatives covalently bonded to the metal surface, a binding layer of a polylactone covalently bonded to the polymerized silane derivatives, and a container layer of a polymer adhered to the binding layer, where the container layer has a biologically active agent(s) releaseably associated with the polymer. The biologically active agent(s) may be about 0.5 to 60% by weight of the container layer.

In a further preferred embodiment, the medical device is, for example, a stent, vascular graft tubing, a blood oxygenator, an intravascular balloon, a catheter, an implantable pulse generator, an electrode, an electrical lead, sutures, a soft or hard tissue prosthesis, or an artificial organ. The container layer and the binding layer include one or more sublayers of one or more polylactone polymers. The polymers may be a lactone co-polymer that may include block copolymers of least one polylactone block.

In another preferred embodiment, the container layer has two or more sublayers of the same or different polymers. The concentration of the biologically active agent(s) in an inner container sublayer may be different than the concentration of the biologically active agent in an outer container sublayer.

In another preferred embodiment, at least one barrier or skin layer is provided on top of the container layer. The composition of the barrier or skin layer may be different from the composition of the outermost container layer sublayer.

DETAILED DESCRIPTION OF THE INVENTION

Figure 1:
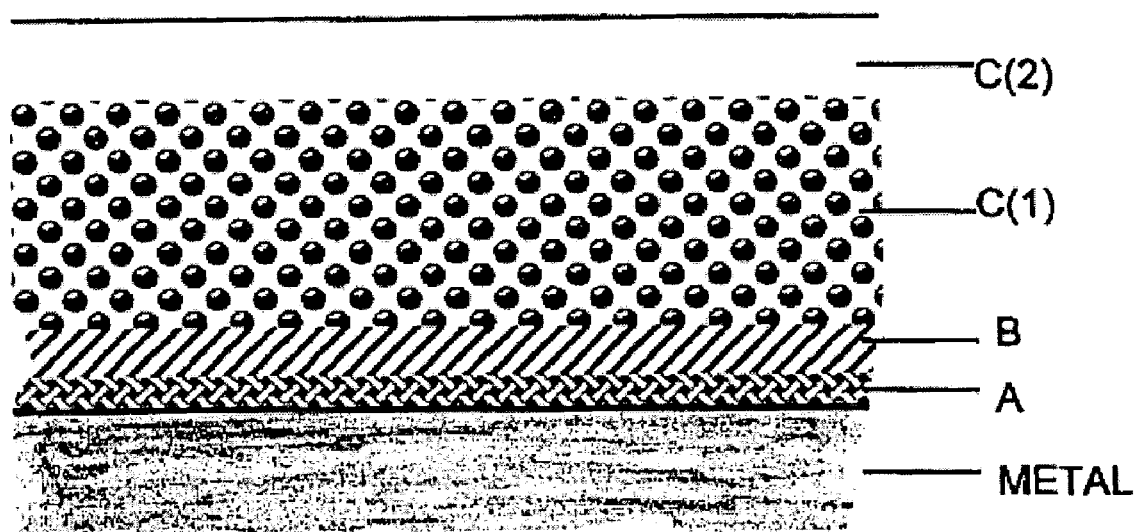
FIG. 1. is a schematic representation of the coated metal surface of the invention.

We recently found the requirements for biologically active compound-releasing polymer coatings for implantable medical devices can be met by using polyester-based polymer coatings. The polymer coating can improve the performance of the device by providing a biocompatible interface between the metal surface and the surrounding tissue, while the biological response of the organism, namely the local response of the surrounding tissue, can be modulated by sustained release of a suitable biologically active agent(s). We found that a low-profile polymer layer, that does not significantly affect mechanical properties of the device and that provides for a long-lasting matrix reservoir for a biologically active agent(s) to be released in a controlled manner, can be produced by a successive deposition of chemically compatible polymers on the metal surface of the implantable device. First, an activating silane derivative interfacing the metal surface is covalently bound to the metal surface to activate the surface and provide for suitable functional groups. Second, a polymer (binding) layer is covalently bound to the activating layer. The covalent binding of the first polymer binding layer provides for good adhesion of any subsequent polymer layers to the surface of the device. This allows for a thin, durable and contiguous film having a release performance which can be adjusted in a reproducible manner. This method is applicable for use with biocompatible, medically applicable polymers, thus making the method suitable for coating medical devices.

Before proceeding further with a description of the specific embodiments of the present invention, a number of terms will be defined.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-pentyl, 2-methylbutyl, n-hexyl,n-decyl, tetradecyl, and the like.

The term "substituted alkyl" refers to (1) an alkyl group as defined above, having from 1 to 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, aminothiocarbonylamino, aminothiocarbonylamio, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; (2) an alkyl group as defined above that is interrupted by 1–5 atoms or groups independently chosen from oxygen, sulfur and —NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or (3) an alkyl group as defined above that has both from 1 to 5 substituents as defined above and is also interrupted by 1 to 5 atoms or groups as defined above.

The term "alkylene" refers to a diradical of a branched or unbranched saturated hydrocarbon chain, preferably having from 1 to 20 carbon atoms, preferably 1 to 10 carbon atoms, more preferably 1 to 6 carbon atoms. This term is exemplified by groups such as methylene (—CH2-), ethylene (—CH2CH2-), the propylene isomers (e.g., —CH2CH2CH2- and —CH(CH$_3$)CH2-) and the like.

The term "substituted alkylene" refers to (1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, aminothiocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; (2) an alkylene group as defined above that is interrupted by 1 to 5 atoms or groups independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or (3) an alkylene group as defined above that has both from 1 to 5 substituents as defined above and is also interrupted by 1 to 20 atoms as defined above. Examples of substituted alkylenes include chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is optionally substituted alkenyl, optionally substituted alkynyl, or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexyloxy, 1,2-dimethylbutoxy, trifluoromethoxy, and the like.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1 to 6, preferably 1, double bond (vinyl). Preferred alkenyl groups include ethenyl or vinyl (—CH═CH$_2$), 1-propylene or allyl (—CH$_2$CH═CH$_2$), iso-propylene (—C(CH$_3$)═CH$_2$), bicyclo[2.2.1]heptene, and the like. In the event that alkenyl is attached to nitrogen, the double bond cannot be alpha to the nitrogen.

The term "substituted alkenyl" refers to an alkenyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, aminothiocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1 to 6 sites of acetylene (triple bond) unsaturation. Preferred alkynyl groups include ethynyl, (—C≡CH), propargyl (or prop-1-yn-3-yl, —CH$_2$C≡CH), and the like. In the event that alkynyl is attached to nitrogen, the triple bond cannot be alpha to the nitrogen.

The term "substituted alkynyl" refers to an alkynyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, aminothiocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, aminothiocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y-Z, in which Y is optionally substituted alkylene and Z is alkenyl, cycloalkenyl, or alkynyl, All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "halogen" or "halo" refers to fluoro, bromo, chloro, or iodo.

The term "acyl" denotes a group —C(O)R, in which R is hydrogen, optionally substituted alkyl, optionally substituted cycloalkyl, optionally substituted heterocyclyl, optionally substituted aryl, or optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, aminothiocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2. Such heteroaryl groups can have a single ring (e.g., pyridyl or furyl) or multiple condensed rings (e.g., indolizinyl, benzothiazolyl, or benzothienyl). Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

"Optional" or "optionally" means that the subsequently described event or circumstance may or may not occur, and that the description includes instances where said event or circumstance occurs and instances in which it does not.

The term "homopolymer" means a polymer derived from one species of monomer.

The term "copolymer" means a polymer derived from more than one species of monomer.

The term "statistical copolymer" means a copolymer consisting of macromolecules in which the sequential distribution of the monomeric units obeys known statistical laws, e.g. the sequential distribution of monomer units follows Markovian statistics.

The term "block copolymer" means a polymer composed of macromolecules consisting of a linear sequence of blocks, wherein the term "block" means a portion of macromolecule comprising many constitutional units that has at least one feature which is not present in the adjacent portions.

The term "polymer matrix" refers to all of the polymer layers or sublayers on the metal surface. This can include activating, binding, container, and/or barrier layers.

The term "amphiphilic copolymer" means a polymer containing both hydrophilic (water-soluble) and hydrophobic (water-insoluble) segments.

The term "polyester" means a polymer with structural units connected by ester bonds, comprising polyesters obtained from dicarboxylic acids and diols, or from hydroxyalkanoic acids by polycondensation, and includes polylactones obtained by ring-opening polymerization of lactones, such as polyglycolides polylactides, polycaprolactone and related copolymers.

The term "metal" means surfaces made of, for example, stainless steel, titanium or tantalum with oxide groups on their surface, as well as other surfaces made of, for example, polymers or glass, with hydroxyl groups or other functional groups that can be transformed to hydroxyl groups on their surfaces. The surface may be of any shape and may be a part of any medical devices. Examples of such devices include both implantable or extracorporeal devices such as vascular graft tubing, blood oxygenators, intravascular balloons, catheters, implantable pulse generators, electrodes, electrical leads, stents, sutures, soft or hard tissue prosthesis, artificial organs and the like. Further, there are likely to be many applications for the coated metal outside the medical field. Accordingly, it will be appreciated by those skilled in the art that the invention described may be applied to many medical devices and in fields outside of medicine where a polymer coated metal surface of the invention may be useful.

A coating composition of this invention is preferably used to coat an implantable medical device that undergoes flexion or expansion in the course of its implantation or use in vivo. The words "flexion" and "expansion" as used herein with regard to implantable devices will refer to a device, or portion thereof, that is bent (e.g., by at least about 30 degrees or more) and/or expanded (e.g., to greater than its initial dimension), either in the course of its placement, or thereafter in the course of its uses in vivo.

Stents are designed to mechanically prevent the collapse and reocclusion of the coronary arteries. The coating composition can also be used to coat stents, which are typically prepared from materials such as stainless steel or tantalum. A variety of stent configurations are known including but not limited to shape memory alloy stents, expandable stents and stents formed in situ e.g., either self-expanding stents (such as the Wallstent variety), or balloon-expandable stents (as are available in a variety of styles, for instance, Gianturco-Roubin, Palmaz-Shatz, Wiktor, Strecker, ACS Multi-Link, Cordis, AVE Micro Stent). Other suitable metals for such stents include gold, molybdenum-rhenuim alloy, platinum-iridium alloy and combinations thereof. See, for example, U.S. Pat. No. 4,733,655, U.S. Pat. No. 4,800,882 and U.S. Pat. No. 4,886,062, all of which are incorporated by reference in their entirety.

The polymer coating or coating composition on the metal surface can be composed of several layers. Referring now to FIG. 1, the metal surface has a first coat (shown as A in FIG. 1), referred to herein as the metal activating layer that is composed of silane polymer derivatives covalently bound to the metal surface. A second layer (shown as B in FIG. 1), referred to herein as the binding layer, is composed of a polylactone covalently bonded to the chemical groupings provided by the silane polymer in the metal activating layer. A third layer (shown as C(1) in FIG. 1), referred to herein as the container layer, is deposited on the surface of the binding layer. The container layer may optionally be composed of one or more sublayers of the same or different polymers. The binding layer and the coating layer may optionally contain one or more biologically active compounds releasably dispersed in the polymer matrix. Once the coated metal surface is placed in an aqueous environment, typically the body fluids, such as blood, lymph or extracellular fluids, the biologically active compounds are released into the aqueous environment. The composition of the binding layer and the container layer may, for example, be adjusted to provide for a controlled release of these compounds into a surrounding aqueous medium and/or to modify the tissue reaction to the presence of the device, for example, to make the surface thromboresistant. The coated metal surface may be composed of two or more sublayers with different functions, optionally the uppermost layer may function as a barrier or skin layer (shown as C(2) in FIG. 1).

The barrier or skin layer can be used to control the biologically active agent release from the polymer matrix. For example, if a single polymer matrix container layer is formed on the surface, a skin layer of the same polymer that is used in the container layer can be added on top of the container layer. This skin layer could either not contain a biologically active agent, or could contain a much lower biologically active agent loading than is present in the container layer, and thus would function as a diffusion barrier for the biologically active agent.

The skin layer can also have different properties, for example, crystallinity, or solubility in solvents, from the container layer. Thus, it may be possible to apply a skin layer using solvents that do not dissolve the underlying container layer and/or extgract the incorporated biiologically active agent.

A skin layer made of a hydrophobic polymer can provide better release control for hydrophilic biologically active agents (or agents with high solubility in water) than a hydrophilic skin. A hydrophilic polymer in the skin layer would facilitate uptake of water into the container layer, increase the hydration, concentration of soluble fraction and, consequently, make the release faster. On the other hand, the agent loading in the container layer is high, close to the percolation limit, a single hydrophilic skin layer may not provide sufficient release control.

The outermost skin or barrier layer can comprise more than one sublayer. The innermost sublayer of the skin layer can be hydrophobic. There may be a hydrophilic sublayer on the outside of the innermost skin sublayer which would provide a biocompatible, nonadsorptive or otherwise biospecific interface between the device and the tissue environment into which the device is placed.

The biologically active (e.g., pharmaceutical) agents useful in the present invention include virtually any therapeutic substance which possesses desirable therapeutic characteristics for application to the implant site. As used herein "biologically active agent" refers to a single biologically active agent or several biologically active agents. It is contemplated that one or more biologically active agents may be releasably associated with the polymers on the metal surface. These agents include, but are not limited to: thrombin inhibitors, antithrombogenic agents, thrombolytic agents (e.g. factor Xa inhibitors), fibrinolytic agents, vasospasm inhibitors, calcium channel blockers, vasodilators, antihypertensive agents, antimicrombial agents, antibiotics, inhibitors of surface glycoprotein receptors, antiplatelet agents, antimitotics, microtubule inhibitors, anti secretory agents, actin inhibitors, remodeling inhibitors, antisense nucleotide, anti metabolites, antiproliferatives (e.g. E2F antisense compounds, Rapamycin (sirolimus), tacrolimus, Taxol, paclitaxol, Cyclin Dependent Kinase inhibitors) anticancer chemotherapeutic agents, anti-inflammatory steroid or nonsteroidal anti-inflammatory agents, immunosuppressive agents, growth hormone antagonists (e.g. PDGF receptor tyrosine kinase inhibitors), growth factors, dopamine agonists, radiotheraputic agents, peptides, proteins, enzymes, extracellular matrix components, ACE inhibitors, free radical scavengers, chelators, antioxidants, antipolyermases, ribozymes, antiviral agents, photodynamic therapy agents, and gene therapy agents.

A preferred biologically active agent is a compound of the following formula:

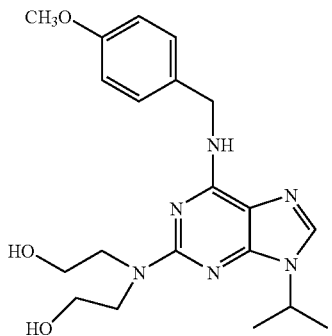

This compound, an anti-proliferative agent known generally as CVT 313, is named 2-{(2-hydroxyethyl)-[9-isopropyl-6-(4-methoxybenzylamino)-9H-purin-2-yl]-amino}-ethanol or also known as 2-diethanolamino-6-(4-methoxybenzylamino)-9-isopropylpurine. It is described in U.S. Pat. No. 5,866,702, which is incorporated by reference herein in its entirety.

Other compounds within the scope of either WO/08/05335 or WO/00/44750, both of which are incorporated herein in their entireties, include 2-[[6-(4-cholorbenzylamino)-9-isopropyl-9H-purin-2-yl]-(2-hydroxyethyl)-amino]-ethanol, also known as 6-(4-chlorobenzylamino)-[bis-(2-hydroxyethylamino)]-9-isopropylpurine;

$N^2$-(2-aminoethyl)-$N^6$-(4-chlorobenzyl)-9-isopropyl-9H-purine-2,6-diamine, also known as 2-(2-aminoethylamino)-6-(4-chlorobenzylamino)-9-isopropylpurine;

2-[[6-(2,5-diflurorbenzylamino)-9-isopropyl-9H-purin-2-yl]-(2-hydroxyethyl)-amino]-ethanol, also known as 6-[(2,5-difluorophenyl)methylamino]-2-[bis-(2-hydoxyethylamino)]-9-isopropylpurine;

2-[6-(2,5-difluror-benzylamino)-9-isopropyl-9H-purin-2-ylamino]-3-methyl-butan-1-ol, also known as 6-[(2,5-difluorphenyl)methylamino]-2-(1-hydroxymethyl-2-methylethylamino)-9-isopropylpurine;

2-{[6-(4-bromophenylamino)-9-isopropyl-9H-purin-2-yl]-(2-hydroxyethyl)-amino}-ethanol, also known as 6-4-bromophenylamino)-2-[bis-(2-hydroxyethylamino)]-9-isopropylpurine;

2-{(2-hydroxyethyl)-[9-isopropyl-6-(quinolin-3-ylamino)-9H-purin-2-yl]-amino}-ethanol, also known as 6-(quinolin-3-ylamino)-2-[bis-(2-hydroxyethylamino)]-9-isopropylpurine;

$N^2$-(2-aminopropyl)-$N^6$-(4-chlorobenzyl)-9-isopropyl-9H-purine-2,6-diamine, also known as 2-(2-aminopropylamino)-6-(4-chlorobenzylamino)-9-isopropylpurine; and 3-{[2-(2-aminoethylamino)-9-isopropyl-9H-purin-6-ylamino]-methyl}-benzoic acid.

Other preferred biologically active agents are adenosine A2a receptor agonists which are known to increase endothelial cell migration and prevent smooth muscle cell growth. Examples of these compounds are represented by the following formulae and are described in detail in the referenced patents and patent applications, each of which is incorporated by reference herein in its entirety.

WO 0078779

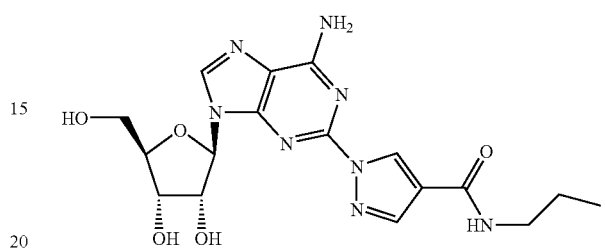

Known as (1-{9-[(4S,2R,3R,5R)-3,4-dihydroxy-5-(hydroxymethyl)-oxolan-2-yl]-6-aminopurin-2-yl}pyrazol-4N-propylcarboxamide, also known as 2-(4-propylaminocarbonylpyrazol-1-yl)adenosine;

WO 0078779

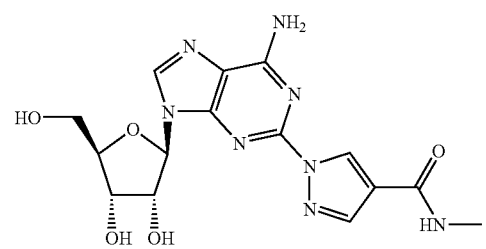

Known as (1-{9-[(4S,2R,3R,5R)-3,4-dihydroxy-5-(hydroxymethyl)-oxolan-2-yl]-6-aminopurin-2-yl}pyrazol-4N-methylcarboxamide, also known as 2-(4-methylaminocarbonylpyrazol-1-yl)adenosine;

U.S. Pat. No. 6,214,807

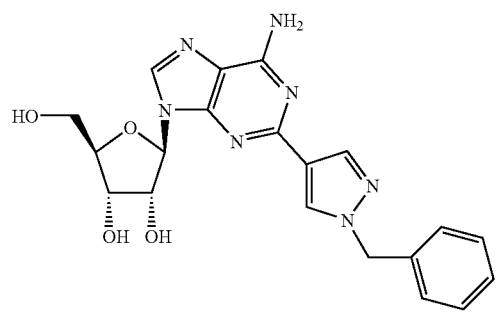

known as (4S,2R,3R,5R)-2-{6-amino-2-[1-benzylpyrazol-4-yl]purin-9-yl}-5-(hydroxymethyl)oxolane-3,4-diol;

U.S. Pat. No. 6,180,615

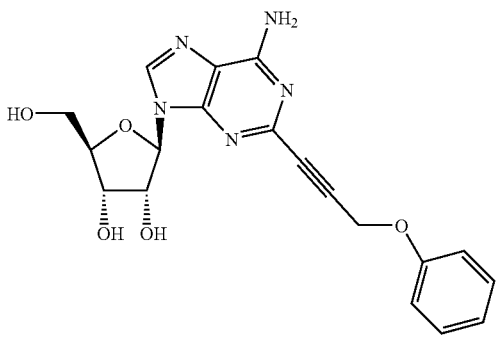

known as (4S,2R,3R,5R)-2-[6-amino-2-(3-phenoxyprop-1-ynyl)-purin-9-yl]-5-(hydroxymethyl)-oxolane-3,4-diol; and
WO 00/78776

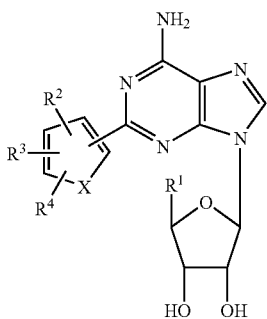

The substituents for the above structure from WO 00/78776 have the following definitions:
wherein X is S, O and $NR^5$;
$R^1$ is —$CH_2OH$, and —$C(=O)NR^7R^8$;
$R^2$, $R^3$, $R^4$ and $R^5$ are each individually selected from the group consisting of hydrogen, halo, $NO_2$, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2$ $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, $OCON(R^{20})_2$, $C_{1-15}$ alkyl, $C_{2-15}$ alkenyl, $C_{2-15}$ alkynyl, heterocyclyl, aryl, and heteroaryl, which alkyl, alkenyl, alkynyl, $C_{1-15}$ alkoxy, aryl, heterocyclyl, and heteroaryl are optionally substituted with from 1 to 3 substituents independently selected from the group consisting of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^{20}SO_2R^{22}$, $OC(O)R^{20}$, $C(O)OCH_2OC(O)R^{20}$, and $OCON(R^{20})_2$ and wherein each optional heteroaryl, aryl, and heterocyclyl substitution substituent is further optionally substituted with halo, $NO_2$, alkyl, $CF_3$, amino, mono- or di-alkylamino, alkyl or aryl or heteroaryl amide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)N(R^{20})_2$, $SR^{20}$, $S(O)R^{22}$, $SO_2R^{22}$, $SO_2N(R^{20})_2$, CN, or $OR^{20}$;

$R^7$ and $R^8$ are each independently selected from H, and $C_{1-15}$ alkyl optionally substituted with from 1 to 2 substituents independently selected from the group consisting of halo, $NO_2$, heterocyclyl, aryl, heteroaryl, $CF_3$, CN, $OR^{20}$, $SR^{20}$, $N(R^{20})_2$, $S(O)R^{22}$, $SO_2R^{22}$, $SO_2N(R^{20})_2$, $SO_2NR^{20}COR^{22}$, $SO_2NR^{20}CO_2R^{22}$, $SO_2NR^{20}CON(R^{20})_2$, $N(R^{20})_2$ $NR^{20}COR^{22}$, $NR^{20}CO_2R^{22}$, $NR^{20}CON(R^{20})_2$, $NR^{20}C(NR^{20})NHR^{23}$, $COR^{20}$, $CO_2R^{20}$, $CON(R^{20})_2$, $CONR^{20}SO_2R^{22}$, $NR^{20}SO_2R^{22}$, $SO_2NR^{20}CO_2R^{22}$, $OCONR^2SO_{20}R^{22}$, $OC(O)R^{20}$, $C(O)OCH_2OC(O)R^{20}$, and $OCON(R^{20})_2$ and each optional heteroaryl, aryl, and heterocyclyl substituent is further optionally substituted with halo, $NO_2$, alkyl, $CF_3$, amino, monoalkylamino or dialkylamino, alkylamide, arylamide or heteroarylamide, $NCOR^{22}$, $NR^{20}SO_2R^{22}$, $COR^{20}$, $CO_2R^{20}$, $CON(R^{20})_2$, $NR^{20}CON(R^{20})_2$, $OC(O)R^{20}$, $OC(O)N(R^{20})_2$, $SR^{20}$, $S(O)R^{22}$, $SO_2R^{22}$, $SO_2N(R^{20})_2$, CN, and $OR^{20}$;

$R^{20}$ is selected from the group consisting of H, $C_{1-15}$ alkyl, $C_{2-15}$ alkenyl, $C_{2-15}$ alkynyl, heterocyclyl, aryl, and heteroaryl, which alkyl, alkenyl, alkynyl, heterocyclyl, aryl, and heteroaryl are each optionally substituted with from 1 to 3 substituents independently selected from halo, alkyl, mono- or dialkylamino, alkyl or aryl or heteroaryl amide, CN, O—$C_{1-6}$ alkyl, $CF_3$, aryl, and heteroaryl; and $R^{22}$ is selected from the group consisting of $C_{1-15}$ alkyl, $C_{2-15}$ alkenyl, $C_{2-15}$ alkynyl, heterocyclyl, aryl, and heteroaryl which alkyl, alkenyl, alkynyl, heterocyclyl, aryl, and heteroaryl are each optionally substituted with from 1 to 3 substituents independently selected from halo, alkyl, mono- or dialkylamino, alkyl or aryl or heteroaryl amide, CN, —O—$C_{1-6}$ alkyl, $CF_3$, and heteroaryl.

In a preferred embodiment, the invention provides for the formation of the binding layer covalently bonded, grafted, or attached, to the metal activating layer. The grafted polymer binding layer is formed by the in-situ ring opening polymerization of lactone monomers initiated by suitable functional groups of the polymer of the metal activating layer and a catalyst added to the polymerization reaction.

Suitable functional groups for initiating the grafting polymerization of lactones ("initiating functional groups") can be created on metal surfaces through the reaction of a metal surface with selected silane derivatives, referred to herein as silane-based activating reagents ("SAR" or "SARs"). SAR is a silane derivative of general formula $(R^2)_3$—$SiR^1$ wherein $R^1$ is independently selected from substituted alkyl, substituted alkenyl, substituted alkynyl, substituted aralkyl, substituted heteroaryl, and substituted alkoxy with the proviso that $R^1$ contains a hydroxy or amino group, or a functional group that can be transformed to a radical that contains a hydroxy or amino group; wherein $R^2$ is independently selected from halo, optionally substituted alkoxy, optionally substituted aryloxy, optionally substituted syloxy, or optionally substituted alkyl with the proviso that all three $R^2$ substituents are not simultaneously substituted alkyl.

Typical SARs can be selected from alkoxysilane derivatives such as tetraalkoxysilanes and organo-trialkoxysilane derivatives. Examples of tetraalkoxysilanes are alkoxysilanes of the formula $Si(OR)_4$ in which the R represents a $C_1$ to $C_4$ alkyl group, such as tetramethoxysilane, tetraethoxysilane, tetra-n-propoxysilane, tetra-n-butoxysilane, and analogues. Typical examples of organo-trialkylsilanes are compounds of a general formula R'—Si—$(OR)_3$ in which the R represents $C_1$ to $C_4$ alkyl groups, and the R' represents a non-hydrolyzable organic substituent.

Also, alkoxysilane derivatives acting as SARs can be formed in situ by the reaction of halosilane derivatives with alcohols. Examples of suitable halosilanes effective in this mode will include tetrachlorosilane, trichloroalkyl silanes and dichlorodialkyl silanes. It becomes obvious that in this mode, the actual SAR is composed of a mixture of chemical species that, in addition to the original halosilane used, will contain tetraalkoxysilanes, trialkoxysilanes as well as dialkoxydialkyl silanes. The silicone industry offers a number of various halosilane and haloalkylsilane as well as tetralkoxy- and organo-trialkoxy-silane derivatives, and many possibilities exist for the organic substituents. See, for example, GELEST Catalogue 2000: Silanes, Silicones and Metal-Organics. Gelest, Inc., Dr. Barry Arkles, Tullytown, Pa., USA.

Figure 2:
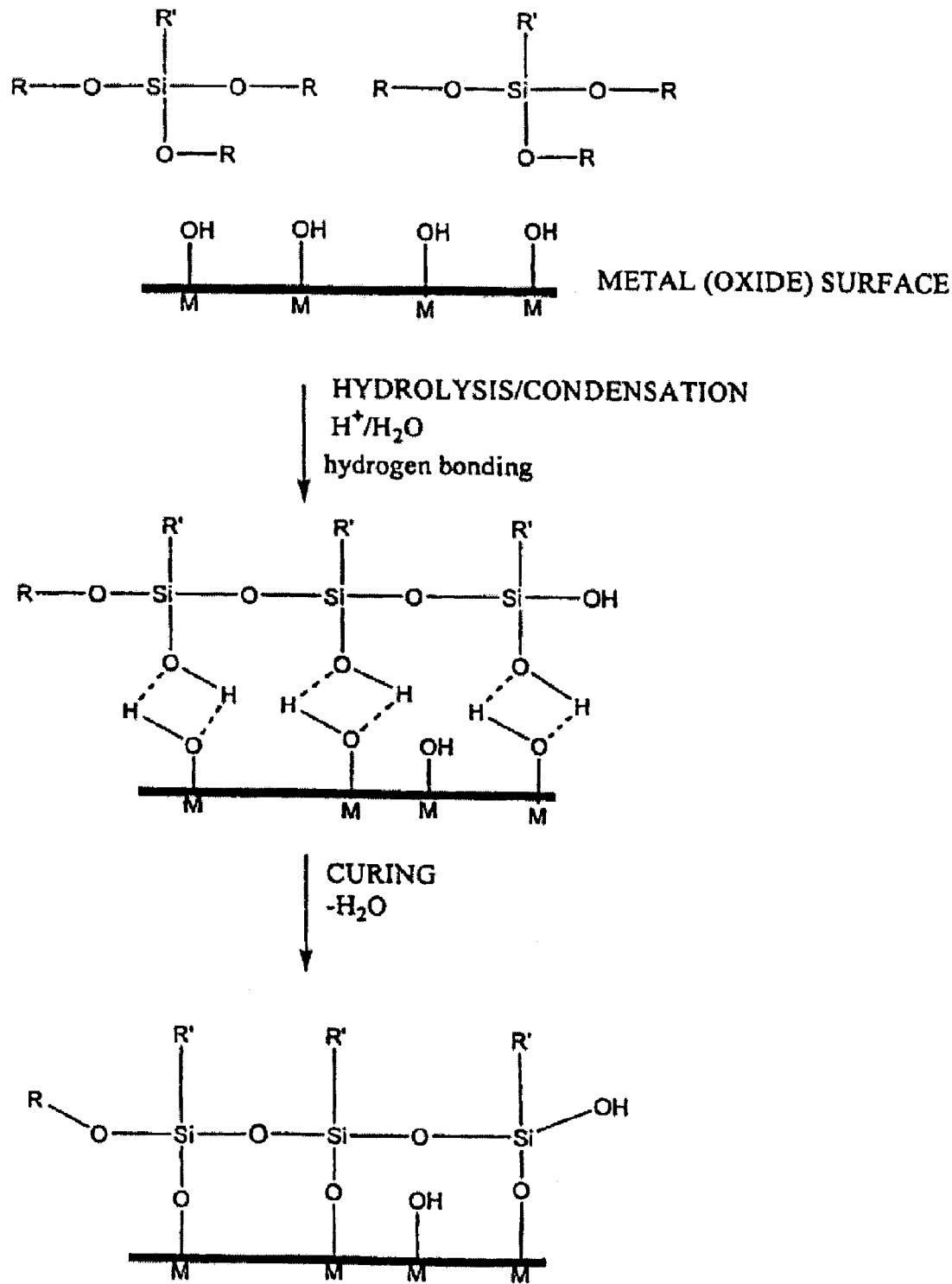
FIG. 2 is a schematic representation of the mechanism and structure involved in the reactive adsorption of alkoxysilane activating reagent on surfaces containing metal oxide groups.

Several structural features of SARs are important to the present invention. It is known that alkoxy groups of alkoxysilanes easily undergo hydrolysis in the presence of water to form silanol groups. Subsequent condensation of silanol groups produces siloxane from silanols. It is also known that through condensation, silanol groups form siloxane chains. Analogously, without wishing to be bound by any theory, it is hypothesized that through the reaction of silanol groups with surface hydroxyl groups of hydrated metal oxides, siloxane bonds between the silicone and metal atoms are formed, thus binding the silane molecules to the surface. At the same time the other alkoxysilane bonds undergo hydrolysis-condensation reaction between silane molecules, thus leading to oligomerization and polymerization of silane and forming a two or three dimensional siloxane network. A schematic representation of the mechanism and structure involved in the reactive adsorption of alkoxysilane SARs on surfaces containing metal oxide groups is shown in FIG. 2. A metal oxide surface comprising metal atoms M having hydroxyl substituents OH is reacted with a SAR having the formula R'—Si(OR)$_3$. Following the removal of water from the reaction, the SAR is covalently bound to the metal surface. In addition, the SAR provides an initiating functional group, such as an alkanol or hydroxyalkyl group, for the initiation of in-situ polymerization of a polyester to provide the binding layer on the metal surface.

While FIG. 2. shows the hydrolysis/condensation reaction achieving the siloxane activating layer as a two dimensional (monomolecular) layer, it is expected that the hydrolytic polymerization of a SAR produces oligomeric species of three-dimensional, cyclic and cross-linked aggregates that interact with the metal surface to provide the siloxane activating layer. Therefore, it is expected that the cross-linked polymerized structure of the siloxane layer has multiple attachment points with the metal, that results in the siloxane layer being firmly adhered to the metal surface.

Suitable functional groups for R' are hydroxyalkyl groups that can form alkoxides through the reaction with a metal catalyst. In this way, the siloxane activating layer with free hydroxyalkyl groups can be prepared by using functional trialkoxysilanes as SAR. Examples of suitable trialkoxysilanes include hydroxyalkyl alkoxysilane derivatives. In addition, the following are examples of commercially available silane-based activating reagents that contain a hydroxy group: N-(3-triethoxysilylpropyl)-4-hydroxybutyramide, N-(3-triethoxysilylpropyl)gluconamide, 3-[Bis(2-hydroxyethyl)amino]propyl-trimethoxysilane, and 3-[Bis(2-hydroxyethyl)amino]propyl-triethoxysilane.

In addition to alkanol and hydroxyalkyl groups, the polymerization of lactones in the presence of suitable metal catalysts can be efficiently initiated also by other strong nucleophiles, in particular by amines, including primary alkyl amines, sterically unhindered secondary amines and compounds containing a nucleophilic amino alkyl chain. Under certain conditions, the reaction of amines with lactones is fast enough to initiate polymerization of lactones in solution or melt. The initial reaction of the amine with lactones, such as lactide, glycolide or ε-caprolactone, provides for amides having an ω-hydroxyalkyl group, such as lactoyllactyl amide, glycolylglycylamide or 6-hydroxycaproyl amide, respectively. Through their ω-hydroxyalkyl groups these amides can form alkoxides with a suitable metal catalyst and in presence of an additional lactone monomer (monomer is defined to include the cyclic dimers of lactic acid and glycolic acid as well as other cylic lactone monomers), polymerization can continue by a propagation reaction, typical for lactone ring-opening polymerization. Suitable reaction conditions for the initiation of the lactone polymerization by alkylamine groups on the surfaces are well compliant with those required for lactone polymerization in general. These conditions include exclusion of water and other protic compounds from the system, except the protic groups presented by activated surface, either in solution or a melt. Typically, an elevated temperture would be beneficial, as it increases the reaction rate of amine and lactone species and the formation of amide bonds. Typical temperature range will be 20 to 250° C., preferably 20 to 120° C., for solution reactions, with the upper limit of this range depending on the solvent and the decomposition temperature of the lactone, while the minimum temperature of the reaction in bulk or a lactone melt will be dependent on the melting temperature of selected lactone monomer.

Thus, the lactone polymerization can be efficiently initiated by the aminoalkyl groups present in the surface activating layer. This allows for the formation of grafting-susceptible functional groups at the metal surfaces by using silane-based activating agents with an amino group. Typical examples of commercially available reagents that may be useful as SARs to be applied in this way include
N-(3-aminoethyl)-3-aminopropyltrimethoxysilane,
3-aminopropyl-trimethoxysilane,
3-aminopropyltriethoxylsilane,
methyl(2-(3-trimethoxysilylpropylamino)-3-propionate,
3-(N-styrylmethyl-3-aminoethylamino)-propyl-trimethoxysilane hydrochloride,
4-aminobutyltriethoxysilane,
3-(3-aminopropoxy)3,3-dimethyl-1-propenyltrimethoxysilane,
N-(6-aminohexyl)aminopropyltrimethoxysilane,
N-(3-trimethoxysilylethyl)ethylenediamine,
N-(2-(N-vinylbenzylamino)ethyl)-3-aminopropyltrimethoxysilane hydrochloride,
1-trimethoxysilyl-2-(aminomethyl)phenylethane,
N-2-(aminoethyl)-3-aminopropyltris-(2-ethyloxy)silane,
3-(N-allylamino)propyltrimethoxysilane,
3-(2-aminoethylamino)propyltrimethoxysilane, and
3-(2-aminoethylamino)propyltriethoxysilane.

In addition to using alkoxy silane and amino silane derivatives to derivative a metal surface, the same result can be achieved by using reactive alkoxysilane intermediates containing a functionalized alkyl group that can be converted to hydroxyalkyl or an amino alkyl group through a subsequent modification reaction with nucleophiles. Typical examples of suitable silylating reactants useful for this mode of the procedure include (3-isocyanatopropyl)triethoxysilane,
(3-thioisocyanatopropyl)triethoxysilane, (3-glycidyloxypropyl)trimethoxysilane,
(3-glycidyloxypropyl)triethoxysilane,
(3-bromopropyl)trimethoxysilane, chloropropyl)trimethoxysilane and analogous compounds.

The isocyanate, thiocyanate, glycidyl or haloalkyl groups present in these reagents can be used for introduction of hydroxyalkyl and/or amine groups by their reaction with diols, amino alcohols, amines and/or diamines. Analogously, alkenyl alkoxysilanes, containing an unsaturated bond in their alkenyl chain, such as allyltrialkoxysilanes, (6-hexen-1-yl)trialkoxysilanes, (7-Octen-1-yl)trialkoxysilanes and analogues, can be modified by the reaction with sulphanyl alkanols and sulphanyl amines. These and other analogous reactions are known to those skilled in the art and are consistent with the scope of the invention.

The following are commercially available reagents that contain a functional group that can be activated to a hydroxy group or amino group through a chemical transformation and which may be useful and silane based activating reagents:
3-chloropropyltrimethoxysilane,
3-mercaptopropyltrimethoxysilane,
3-glycidoxypropyltrimethoxysilane,
vinyltris(2-methoxyethoxy)silane,
vinyltrimethoxysilane,
vinyltriethoxysilane,
allyltriethoxysilane,
2-(3,4-epoxycyclohexyl)ethyltrimethoxysilane,
3-chloropropyltriethoxysilane,
2-cyanoethyltriethoxysilane,
3-cyanopropyltrimethoxysilane,
vinyltriphenoxysilane,
chloromethyltriethoxysilane,
2-cyanoethyltrimethoxysilane,
3-acetoxypropyltrimethoxysilane,
3-thiocyanatopropyltriethoxysilane,
3-isocyanatopropyltrimethoxysilane,
(p-chloromethyl)phenyltrimethoxysilane,
tetraallyloxysilane,
triethoxysilylpropylethylcarbamate,
allyltrimethoxysilane,
3-bromopropyltrimethoxysilane,
3-mercaptopropyltriethoxysilane,
4-((chloromethyl)phenethyl)trimethoxysilane,
2-carbethoxyethyltriethoxysilane,
allyltris(trimethylsiloxy)silane,
diethylphospatoethyltriethoxysilane,
3-iodopropyltrimethoxysilane,
8-bromooctyltrimethoxysilane,
diethyl(triethoxysilylpropyl)malonate,
1-methyl-4-(1-methyl-(2-triethoxysilyl)ethyl)-cyclohexene,
3-butenyltriethoxysilane,
4-(trimethoxysilyl)-1-butene,
(2-(3-cyclohexenyl)ethyl)triethoxysilane,
4-(trimethoxysilyl)butane-1,2-epoxide, 2-(3,4-epoxycyclohexyl)ethyltriethoxysilane,
triallyloxyvinylsilane,
5-(bicycloheptenyl)triethoxysilane,
acetoxymethyltriethoxysilane,
acetoxymethyltrimethoxysilane,
(p-chloromethyl)phenyl-tri-N-propoxysilane,
3-(triethoxysilyl)-2-methylpropylsuccinic anhydride,
2-(triethoxysilylethyl)-5-(chloroacetoxy)bicycloheptane,
2-(chloromethyl)allyltrimethoxysilane,
2-carboethoxytriethoxsilane,
11-cyanoundecyltrimethoxysilane,
5,6-epoxyhexyltriethoxysilane,
mercaptomethyltrimethoxysilane,
3-(N-cyclohexylamino)propyltrimethoxysilane,
triethoxysilylpropylmaleamic acid,
3-bromopropyltriethoxysilane,
3-trifluoroacetoxypropyltrimethoxysilane,
vinyltrichlorosilane,
allyltrichlorosilane,
(3-acetoxypropyl)trichlorosilane,
3-chloropropyltrichlorosilane,
3-cyanopropyltrichlorosilane,
3-chloropropyltrichlorosilane,
2-(carbomethoxy)ethyltrichlorosilane,
acetoxyethyltrichlorosilane,
3-bromopropyltrichlorosilane,
7-octenyltrichlorosilane,
[2-(3-cyclohexenyl)ethyl]trichlorosilane,
(p-chloromethyl)phenyltrichlorosilane,
2-chloroethylsilane,
bicycloheptenyl-2-trichlorosilane,
3-(trichlorosilyl)cyclopentene,
(3-cyanobutyl)trichlorosilane,
3-cyclohexenyltrichlorosilane,
(chloromethyl)phenethyl)trichlorosilane,
5-hexenyltrichlorosilane,
2-(chloromethyl)allyltrichlorosilane,
11-bromoundecyltrichlorosilane,
p-(T-butyl)phenethyltrichlorosilane,
2-(chloromethyl)propyltrichlorosilane,
8-nonenyltrichlorosilane,
10-undecenyltrichlorosilane,
(4-cyclooctenyl)trichlorosilane,
14-tetradec-1-enyltrichlorosilane,
2-bromoethyltrichlorosilane,
methacryloxypropyltris(methoxyethoxy)silane,
methacryloxypropyltris(trimethylsiloxy)silane,
3-methacryloxypropyltris(vinyldimethylsiloxy)silane,
(3-acryloxypropyl)trimethoxysilane, and
methacryloxypropyltriethoxysilane.

The modification reactions of reactive silane intermediates can be conveniently performed in conjunction with the silylation of the metal surfaces. Accordingly, the silylation reaction is carried out with the SAR having a reactive silane intermediate in the presence of nucleophiles such as diols, amino alcohols or amines. Otherwise, the silylation reaction can be performed in one step and, subsequently, the modification with nucleophile reactants can be applied on the silylated metal surfaces.

To treat metal surfaces, the SAR can be applied in solution or in a vapor phase. A variety of solvents and solvent compositions can be used. In this respect, numerous references are available, teaching the use of silane derivatives in sol-gel processes and as adhesion promoters in corrosion protection. For a review of this art see for example, Iler, R. K. The Chemistry of Silica, Wiley, New York, 1979; Brinker, C. J., Scherer, G. W., Sol-Gel Science: the Physics and Chemistry of Sol-Gel Processing, Academic Press, New York, 1990; Jang, J., Kim, E. K. Corrosion Protection of Epoxy-Coated Steel Using Different Silane Coupling Agents, *J. Applied Polym. Sci.* (1999), 71:585, each of which is incorporated herein by reference in its entirety.

It is expected that the siloxane polymer is bonded to the metal surface through a siloxane bond to the oxygen atom of the metal oxide. Therefore, the presence of metal oxide on the surface is expected to be important. Most of the metal articles, due to their contact with air, already exhibit a layer of metal oxide on their surface, which would be sufficient to carry out the procedure according to this invention. However, a treatment of the metal surface by an oxidizing agent prior to application of SAR, for example, the treatment of the metal surface by an oxidizing agent as a part of a cleansing procedure, is consistent with this invention.

The polymerization of alkoxysilane involves the hydrolysis of alkoxides as one of the reaction steps. Therefore, the presence of water molecules in the reaction medium is expected to be important. Accordingly, SAR may be applied in a solution which contains water either added intentionally, or present as an impurity, as it is common in commercial grades of many solvents. Water can also be added to the system by letting it adsorb on the metal surface to be treated, either by exposing the oxidized surface to the water vapors or, in some cases, the amount of water adsorbed from the air in contact with metal will be sufficient.

The polymerization of alkoxysilanes involves condensation reactions including silanols, alkoxides and metal oxides, during which water and/or alcohol molecules are liberated. Therefore, conditions enhancing the removal of the leaving compounds may be employed. Such conditions include treatment of silanized surfaces at elevated temperature or the application of a vacuum.

Following the silylation of the metal surface, a binding polymer layer is applied to the surface. To apply the polymer of the binding layer, a binding or grafting reaction is carried out by exposing the SAR-activated surface to a solution of lactone and the catalyst in a suitable aprotic solvent, or to a mixture of catalyst and a lactone in bulk. In the initiation reaction of the grafting polymerization, the first lactone monomer forms a covalent bond with the functional group of the SAR bound to the metal surface. In subsequent steps, the polylactone chain propagates by a stepwise addition of lactone monomer. The resulting polymer molecules thus remain covalently bound to the surface through its initial structural unit. The chemical mechanisms that apply in the polymerization grafting used in this embodiment are analogous to those that apply in the ring-opening polymerization of lactones in bulk or a solution. The field of lactone polymerization either in bulk or a solution is well described in numerous literature and principles of these reactions are known to those, skilled in the art. Examples of the most frequently used polymerization reactions can be found in Dubois, P. et al., Aluminium Alkoxides: A Family of Versatile Initiators for the Ring-Opening Polymerization of Lactones and Lactides, *Makromol. Chem., Macromol. Symp.* (1991) 42/43:103–116; Inoue, S., Coordination Ring-Opening Polymerization. *Prog. Polymer. Sci.* (1988) 13:63–81; Jonte, J. M. et al., Polylactones. 4. Cationic Polymerization of Lactones by Means of Alkylsulfonates. *J. Macromol. Sci. -Chem.* (1986) A23:495–514; Kricheldorf, H. R. et al., Anionic and Pseudoanionic Polymerization of Lactones—a Comparison. *Makromol. Chem., Macromol. Symp.* (1990), 32:285–298; Kricheldorf, H. R. et al., Poly (Lactones). 9. Polymerization Mechanism of Metal Alkoxide Initiated Polymerizations of Lactide and Various Lactones, *Macromolecules* (1988) 21:286–293; and Lofgren, A. et al., *J. M. S. -Rev. Macromol. Chem. Phys.* (1995) C35: 379–418, each of which are incorporated by reference in their entirely.

It is known that typical initiating species in lactone polymerization are metal alkoxides which can be added to the reaction mixture or are formed in situ from the metal catalyst and alkanols or other hydroxyl-containing compounds. According to a preferred embodiment of the invention, only the functional groups of the metal activating layer bound to the metal surface are to be involved in the initiation of lactone polymerization. Thus, during the initiation of the grafting polymerization, the hydroxyl and/or amine groups present in the siloxane polymer will become acylated by lactone monomer and, subsequently, through the continuing chain addition of monomer, the polyester chain will grow anchored by its initial acyl bond to the siloxane functional groups. This method of polymerization is hereafter termed a grafting polymerization.

Accordingly, in contrast to the usual lactone polymerization in bulk or a solution, it is preferred in the present invention that the addition of free species, that can act as initiating species of lactone polymerization, into the polymerization medium is avoided. The incidental presence of these compounds or protic impurities, which may lead to the formation of free initiating species in the medium, could initiate the growth of free polylactone polymers in the bulk (or a solution) which will not be bound to the surface. Such free polymer chains will be inefficient in formation of the binding layer, as they would be easily washed out by a polymer solvent.

Suitable monomers in grafting polymerization are lactones. Typical examples of lactones include four to seven-membered lactones, for example, the families of compounds comprising oxetan-2-one and 4-alkyl-oxetan-2-one, dihydrofuran-2-one and 5-alkyl-dihydrofuran-2-one, tetrahydropyran-2-one and 6-alkyl-tetrahydropyran-2-one, oxepan-2-one and 7-alkyl-oxepan-2-one, 1,4-dioxan-2,5-dione, 3,6-alkyl-1,4-dioxan-2,5-dione, 1,3-dioxepan-2-one, 1,3-dioxan-2-one, 1,3-dioxolan-2-one, 1,5-dioxepan-2-one, 1,4-dioxepan-2-one, 1,3-dioxepan-4-one, and their substituted analogues, wherein the alkyl is C1–C10 alkyl or a substituted alkyl. In a prefered embodiment of the invention the lactone monomer comprises lactide (3,6-dimethyl-1,4-dioxane-2,5-dione) in its various enantiomeric forms (L-lactide, D-lactide, meso-lactide and their mixtures), glycolide (1,4-dioxane-2,5-dione), and ε-caprolactone.

For the binding layer, combinations of lactone monomers may be used to provide for grafting copolymerization. These copolymers can be made available with different ratios of the co-monomers. Both the homopolymers and copolymers can be used in different molecular-weight ranges. Preferably, the lactone copolymer includes one of poly(L-lactide-co-D-Lactide), poly(L-lactide-co-glycolide), poly(D-lactide-co-glycolide), poly(D,L-lactide-co-glycolide), poly(lactide-co-caprolactone), poly(lactide-co-dioxanone), and poly(lactide-co-dioxepanone).

The grafting of lactone molecules onto the functional groups at the surface can be carried out by applying the coordination-insertion mechanism of lactone polymerization. This method is particularly suitable, because it does not involve strongly acidic or alkaline conditions or reactants. Therefore, the metal siloxane bonds of the activating polysiloxane layer are preserved.

In the coordination-insertion mechanism, the polymerization process starts by the reaction of hydroxyalkyl groups attached to the surface with a metal catalyst, thus leading to the formation of metal-alkoxides with a covalent or coordination metal-oxygen bond and energetically favorable free p- or d-orbitals. The coordination of the metal atom of the alkoxide with the the oxygen of the lactone molecule leads to the weakening of the acyl bond of the lactone ring which, subsequently, opens and is inserted between the metal and oxyalkyl residue, thus propagating the metal-alkoxide grouping. By repeating this step with other lactone molecules, the polymer chain propagates. Suitable metal catalysts in this mechanism are metal carboxylates, alkyl metallic and halide metallic compounds. Typical examples of suitable catalysts include tin(II), antimony, zinc, iron or calcium carboxylates, organo-aluminum and organo-tin compounds, tin, zinc, titanium, zirconium, ytterbium halides, etc. In general, the classes of catalysts that can be used are generally known to those skilled in the art for the polymerization of lactones in bulk or solution. In applications related to medical devices, non toxic and low-toxicity catalysts, such as tin(II), zinc, calcium and iron carboxylates, and alkyl aluminum compounds, are preferred. Examples of the preferred catalysts may include tin(II) 2-ethyl hexanoate, tin(II) lactate, zinc(II) 2-ethylhexanoate, zinc(II) lactate, triethyl aluminum and diethylaluminum chloride.

Typical examples of aprotic solvents for carrying out the grafting reaction in solution include ethers (e.g., tetrahydrofuran, dioxane, di(ethylene glycol), diethyl ether), ketones (e.g. ethylmethyl ketone, diisobutyl ketone) and aromatic hydrocarbons (e.g. toluene, xylene), and mixtures of these solvents. Those skilled in the art can readily identify other solvents which would be useful for the grafting reaction.

The concentration of the lactone in the solution should be such that there is sufficient surplus of the mole amount of lactone over the mole amount of initiating functional groups on the activated metal surface to be grafted. These conditions are easily achieved for a wide range of lactone concentrations. The preferred concentration of lactone is such that the mole amount of lactone is higher than the amount of surface functional groups. More preferably, the mole amount of lactone should be at least ten times higher than the amount of surface functional groups. In practice, these conditions will be well achieved with the weight concentration of lactone in the solution being in a range of 0.1 to 50%, typically, in a range of 0.1 to 10% (w/w).

The grafting reaction can be carried with a wide range of catalyst concentrations. It has been found that the most efficient mole amount of the catalyst is the mole amount equal to or higher than the mole amount of functional initiating groups on the surface to be grafted. The mole ratio of the catalyst to lactone is not specifically limited. The selection of a suitable mole ratio is guided by practical reasons and type of catalyst used, taking into account possible toxicity of some catalysts, that would call for minimizing the catalyst concentration on one hand, and the fact that the rate of polymerization increases with the increasing catalyst/lactone ratio on the other. A preferred catalyst-to-lactone mole ratio is in a range of 1/10 to 1/1000.

In addition, the grafting reaction can be carried out in the absence of solvent, i.e., in the mixture formed by a lactone in bulk and a catalyst. In this mode of the invention, the temperature of the reaction is preferably such as to keep the lactone in a liquid state, such as above the melting temperature of the lactone. The reaction in lactone melt is carried out for the time necessary to form a binding layer of a desired thickness. After carrying out the reaction for a given time, the surface is removed from the melt, the residual lactone is washed from the surface by a suitable solvent and the grafted surface is dried.

The polylactone-grafted metal surfaces exhibit novel properties affecting their surface energy, wettability, adsorptivity, and their interactions in the biological environments. Such interactions include protein adsorption, thrombogeneity, platelet adhesion and activation, and modified tissue reactions.

The covalently grafted polymer binding layer is firmly bonded to the metal surface. As a result of this covalent binding the grafted polymer layer is resistant to removal by treatment with solvents. However, thermodynamically good solvents can penetrate into the grafted polymer layer, causing the polymer chains to expand and thus become capable of adsorbing or accumulating compounds from solutions. The adsorbed or accumulated compounds can be either biologically active agents or molecules of another polymer that have a similar or a compatible chemical structure or that are miscible with the grafted polymer. These features of the grafted polylactone layer can be employed either for direct incorporation of biologically active agents to be released from the layer or for the design and attachment of other subsequent, well adherent, high-capacity polymer layers incorporating the agents.

When the polylactone binding layer grafted to the metal surface is soaked in a solution of the biologically active agent in a solvent appropriate for a given polylactone, the solvent swells the grafted polymer and makes it possible for the biologically active agent to penetrate the polymer layer. After the solvent is stripped off by evaporation, which can be either spontaneous or assisted by the application of vacuum, the biologically active agent, being less volatile than the solvent, is embedded in the polymer, the chains of which have condensed, thus becoming closely packed into a compact matrix upon removal of solvent. Later, when the surface is put into an environment which is not a good solvent for the polymer, such as the aqueous environment of tissue fluids, the condensed polymer chains prevent the molecules of the agent from being rapidly dissolved or diffused into the aqueous medium. This action extends the time period within which the agent is released.

According to a preferred embodiment of the invention, the polylactone binding layer grafted to the metal surface is soaked in a solution formed by a good solvent for polylactone, a biologically active agent, and a polymer that is chemically compatible or miscible with the grafted one. The polymer deposited from the solution on the top of the grafted binding layer forms the container layer on the surface. When the surface is soaked in the solution, the solvent swells the grafted polymer binding layer and the polymer molecules which are to form the container layer penetrate the swollen grafted binding layer and entangle with the grafted chains. Additionally, the biologically active agent in solution may become embedded in the binding layer. In practice, the solution containing the polymer of the container layer is applied to form a liquid film on the top of the grafted binding layer surface. After the solvent has been evaporated from the solution, the solidified polymer film of the container layer will become well joined with the underlying grafted binding layer due to mutual entanglements of polymer chains. Layers of polymers of various controllable thickness and composition can be applied to the anchoring grafted binding layer to form sublayers of the container layer. Biologically active agents contained in the solution with the polymer remain embedded in the solidified polymer container layer film. It is also possible to soak the polylactone binding layer grafted to the metal surface in a solution of a biologically active agent, using a good solvent for both the grafted polylactone and the biologically active agent. The biologically active agent will penetrate into the grafted polymer binding layer which is being swollen by the solvent and, after evaporation of the solvent, the biologically active agent will then remain embedded in the grafted polymer binding layer.

Biologically active agents can be released from the solidified film of binder and/or container layer into the aqueous environment by their gradual dissolution and diffusion through the polymer matrix. This release may also be accomplished by polymer degradation alone, or in addition to the diffusion of the biologically active agent through the polymer matrix. By controlling the thickness and composition of the polymer layers (e.g., binding and container), the capacity of the system for the loaded biologically active agent and the rate of its release can be controlled. Accordingly, the biologically active agent is releasably associated with the polymer. When the coated metal surface is used as an implantable medical device, the biologically active agent can be locally released from the polymer matrix in a controlled manner into a patient receiving the medical device.

In one embodiment of the invention if lactide is used for grafting the binding layer to the activated metal surface, a poly(lactide) serves as the container layer. In this case, the same chemical structure of polymers in both the binding and container layers assures their good adhesion. Analogously, when a poly(ε-caprolactone) layer is desired to be the main component of the container layer, its good adhesion to the surface can be achieved by using ε-caprolactone as a monomer in the grafting polymerization of binding layer. Accordingly, a stable and well adherent polymer matrix can be achieved through various combinations of the compositions of the container layer and the binding layer using a variety of lactone polymers and copolymers by taking into account the chemical compatibility or miscibility of the polymers of both layers.

In various embodiments of the invention, the physical properties of the polymer coating matrix can be modified while maintaining the compatibility of the binding layer and the container layer. The composition of the polymers in the layers can be adjusted by using either a chemical modification, such as statistical and block copolymers, or a physical modification, such as blends or composites.

The polymers used for formation of the container layer include lactone homopolymers, examples of which include poly(L-lactide), poly(D-lactide), polyglycolide, poly(ε-caprolactone), poly(p-dioxanone), poly(dioxepanone), poly(trimethylene carbonate) statistical copolymers of lactones, examples of which may include poly(L-lactide-co-D-Lactide), poly(lactide-co-glycolide), poly(D,L-lactide), poly(lactide-co-caprolactone), poly(lactide-co-trimethylene carbonate) and other combinations of lactones that can be typically derived from lactone monomers. These copolymers can be made with different ratios of the co-monomers. Both the homopolymers and copolymers can be used in different molecular-weight ranges.

The container layer can also include a block copolymer containing at least one polylactone block. The other blocks of the copolymer can be based on polylactone or another chemical structure such as polyether, poly(amino acid), poly(acrylate), poly(methacrylate), polybutadiene, polyisoprene, etc. Typical examples of compositions of suitable block copolymers comprise polylactide/polycaprolactone, polylactide/poly(ethylene oxide), polycaprolactone/polybutadiene, polycaprolactone/poly(ethylene oxide), polylactide/poly(amino acid). The block copolymers can exhibit different ratios of block lengths, different numbers of blocks, and different molecular weights.

It is anticipated that the properties of copolymers may vary with different ratios of co-monomers in the copolymers as well as they may vary with molecular weight. The invention is not limited to any particular copolymer composition or a molecular weight range. In addition to changing the chemical constitution of the polymer molecules, the properties of polymer films formed can be modified also by blending different types of polymers, i.e. homopolymers, statistical and block copolymers.

In the selection of solvent for the polymer of the container layer and the biologically active agent, one has to take into account the solubility of a given polymer composition in the solvent of choice. Typically the selection of solvent will vary with various types of polymers used for formation of the container layer. For instance, when polymers with low degree of crystallinity are used, such as poly(D,L-lactide), and lactide copolymers, suitable solvents can be chosen from medium interactive solvents, comprising ethers, ketones, amides, aromatics and chlorinated hydrocarbons. Typical examples of suitable solvents include tetrahydrofuran, dioxane, toluene, acetone, N,N-dimethylformamide, dimethylsulfoxide, chloroform, dichloromethane, and dichloroethane, as well as mixed solvents comprising various combinations of these and other solvents. When polymers with high degree of crystallinity are used, such as polyglycolide, poly(L-lactide) etc., strongly interacting solvents, such as hexafluoropropanol or trifluoroacetic acid, may be needed.

The selection of the solvent will also be made with respect to the solubility of the biologically active agent to be incorporated. Depending on the type of biologically active agent, various approaches can be adopted. In one mode, the selected solvent may be a good solvent for both, the polymer and biologically active agent. In this approach, the mixture of the polymer and the biologically active agent will be applied in a form of a homogenous solution. In another mode of the procedure, a good solvent for the polymer, which, however, does not dissolve the biologically active agent, can be chosen. In this approach the polymer-agent composition will be applied in a form of a heterogeneous suspension of the particles of the biologically active agent in the polymer solution. It becomes apparent, that there can be various intermediate modes, in which the biologically active agent is either only partly soluble in the selected solvent, or it reaches its solubility limits during evaporation of the solvent after its deposition. The outcomes based on these considerations will influence the phase structure and morphology of the biologically active agent dispersion in the container layer and, consequently, the parameters controlling the rate and duration of the biologically active agent release. The invention is not particularly limited to any of these approaches.

There are many ways to apply the polymer solution to become the container layer on the polymer-grafted binding layer surface of a metal article. Procedures commonly known in coating applications can be used as long as they provide for good wetting of the binding layer surface by the polymer solution. Preferably the application procedure will allow for the control of the parameters of the polymer layer such as layer composition, thickness, and integrity. Thus, the polymer solution can be applied on the binding layer surface by dipping the surface to be coated in the polymer solution, by spraying the polymer solution on the binding layer surface, by pouring or spreading the solution onto the binding layer surface, or any other technique known to those skilled in the art. After the solution is applied to the binding layer surface, excess solvent is evaporated. Various means to control the amount of solution remaining on the binding layer surface before and during evaporation of the solvent can be used to control the thickness and homogeneity of the container layer. These procedures include spreading the solution and stripping its excess by a centrifugal force, spreading and removing the excess solution by a spreading tool, dosed spraying, and those procedures that are generally known in the art of polymer coating.

In a preferred embodiment of the invention, the compositions of the grafted binding layer and the container layer are chosen such that at least one polymer component of the container layer is well compatible with the polymer of the binding layer. Compatibility between the layers improves the wetting of the binding layer by the solution of the container layer and facilitates the formation of a contiguous and well-adherent polymer matrix. Thus, the polymer film of the container layer may be designed so that it has the desired composition, thickness and physical properties, such as morphology, phase structure, glass transition, and crystallinity, while being capable of being applied in a simple coating technique.

According to another embodiment of the invention, the polymer solution of the container layer may contain one or more biologically active agents that are intended to be released when a device with the polymer matrix is placed in an appropriate aqueous environment. The biologically active agent may be either dissolved in the solution containing the polymer, or it can be dispersed in the solution of the polymer in a form of solid particles. In either case, the biologically active agent will become incorporated in the polymer film during the solidification of the polymer layer by solvent evaporation.

The rate of the release of the biologically active agent can be controlled through the composition and other parameters of the polymer container layer. The parameters such as layer thickness, morphology, phase structure, hydrophobicity, degree of hydration, the ratio of crystalline and amorphous phases, glass-transition temperature of the polymer are relevant to release control. These parameters can be controlled through the selection of polymers and their application procedures.

It is known that the stereoregular homopolymers, such as poly(L-lactide) or poly(D-lactide) exhibit a semicrystalline structure, with the content of crystalline phase typically up to about 60 percent of the polymer. In one mode of performing the invention, by using copolymers of D- and L-lactide and by changing the ratio of L and D stereoisomers, the content of the crystalline phase will change from a highly crystalline material for pure poly(L-lactide), or pure poly(D-lactide), to fully amorphous material for the ratio of stereoisomers approaching 1:1. Since the diffusion of compounds within and out of the polymer matrix depends on the mobility and rotational freedom of polymer chains, which mobility and rotational freedom are strongly hindered in the crystalline state of the material, the diffusion of biologically active agents through the crystalline phase of the polymer matrix will be hindered. Thus, the volume fraction of the crystalline phase in the polymer matrix will affect diffusion of the biologically active agent. Therefore, the release of the biologically active agent can be controlled by using a poly(L-lactide-co-D-lactide) in which the mole fraction of either of the L-lactide or D-lactide units in the copolymer is greater than about 0.7. This allows for the copolymer to maintain a semicrystalline structure and inhibit the diffusion of the biologically active agent.

The crystalline phase of the polymer is formed by organized and tightly packed polymer chains. The biologically active agent dispersed in the polymer matrix is mostly excluded from the crystalline phase. Consequently, a given amount of the biologically active agent accumulates predominantly (in a higher concentration) in the remaining amorphous phase of the polymer matrix. Thus a depot of biologically active agent can be formed from which the biologically active agent is released by diffusion through the amorphous phase intertwining the crystalline domains. The flux of the agent from the system can additionally be controlled by deposition of two or more subsequent sublayers of the polymer container layer in which the inner sublayer serves as a depot of biologically active agent (a container sublayer) and the outermost sublayer of the container layer serves as a diffusion-rate controlling barrier, also part of the container layer and more particularly referred to as a skin layer.

In a preferred embodiment of the invention, the inner container sublayer is a semicrystalline poly(L-lactide-co-D-lactide) in which the mole fraction of either of the L-lactide or D-lactide units in the copolymer is greater than about 0.7, and an outer container sublayer is an amorphous polymer such as poly(L-lactide-co-D-lactide), poly(lactide-co-p-dioxanone), or poly(lactide-co-dioxepanone), or mixtures thereof. Other preferred embodiments include an inner container sublayer having a semicrystalline polymer, or a semicrystalline mixture of polymers, wherein the polymer or polymers are poly(L-lactide), poly(glycolide), poly(lactide-co-glycolide) or a poly(L-lactide-co-D-lactide) with the mole fraction of L-lactide structural units in the range of 0 to 0.3 or 0.7 to 1.0, and the outer container sublayer is an amorphous polymer such as poly(L-lactide-co-D-lactide), poly(lactide-co-p-dioxanone) with the mole fraction of the L-lactide structural unit in the range of 0.3 to 0.7, or poly(lactide-co-dioxepanone).

Further, other blends can be used in the container or optional barrier layers. While polyesters like polylactide (PLA) and polycaprolactone (PCL) are rather hydrophobic polymers, exhibiting a low degree of hydration, poly(ethylene oxide) (PEO) is a hydrophilic polymer and is soluble in water. Thus a polymer film composed of polylactide and a polylactide/poly(ethylene oxide) block copolymer can form a two-phase system with a hydrophobic phase, rich in PLA, and a hydrophilic phase, rich in PEO. The degree of hydration of the polymer and, consequently, the permeability of the polymer film for water and incorporated hydrophilic biologically active agents can be increased by increasing the fraction of the hydrophilic phase, such as PLA/PEO block copolymer, in the blend. Thus, through the variation of the PLA/PEO copolymer in the film the release rate of certain biologically active agents can be controlled. Similarly, depending on the degree to which a biologically active agent is hydrophilic or hydrophobic, other combinations of polymers can be used to control the release rate of biologically active agents.

Still further, while polylactide has a glass-transition temperature ($T_g$) in the range of 55 to 60° C., the $T_g$ of poly(p-dioxanone) can be in the range of −15° C. to −20° C. Copolymers of lactide and p-dioxanone can be made, which are crystalline and yet have a glass transition temperature below 37° C., thus affording a pliable polymer container film with good permeability for incorporated compounds. In another embodiment of the invention, the container layer can be applied either in one step as a single layer or in several consecutive steps to produce multiple sublayers. The composition in each layer or sublayer of the container layer can be the same or different. In a preferred embodiment, the first sublayer of the container layer to be applied is compatible with the grafted binding layer. In following steps, additional polymer container sublayers with different compositions can be applied on top of the first container sublayer. In this way, a container layer polymer film with optimized bulk (internal sublayer) and surface (external sublayer) properties can be designed using different polymer compositions for bulk and surface sublayers.

It is expected that the rate of permeation of a compound, such as a biologically active agent, through the polymer layers depends on the concentration of the compound in the polymer matrix. Accordingly, in a preferred embodiment of the invention, the bulk and surface sublayers of the container layer polymer film can differ in the content of the releasably incorporated biologically active agent. Thus, the bulk layer or sublayer of the polymer with a high content of the biologically active agent can be covered by a surface layer (or layers or sublayers) of a polymer with a low content of the biologically active agent. Using this approach, the content of the biologically active agent in the bulk layer or sublayer can be increased up to, or above, a percolation threshold for the diffusion of the biologically active agent through the polymer matrix, yet the release of the biologically active agent from the film can still be controlled by the container layer surface polymer layer. Thus, the release rate of the biologically active agent can be controlled by the composition and thickness of a container layer surface layer or layers. In a polymer matrix with more than one container layer, the outermost container sublayer may function as a skin, i.e., this layer either does not include the biologically active agent or its concentration in the skin layer is significantly lower than that in the underlying container sublayers. The skin layer can be used to further control the release of the biologically active agent. Additional skin layers may be applied to improve the biocompatibility to the device.

The polymer layers may contain up to about 60% of the biologically active agent by weight, depending on the physical properties of the biologically active agent, such as its solubility in water, its crystalline forms and compatibility with the polymer matrix forming the layer. It is anticipated that a content of biologically active agent close to the upper limit of this range can be more easily achieved with low-solubility compounds, which at the same time exhibit a high adherence to the polymer of the container layer. On the other hand, biologically active agents with high solubility or pure miscibility with the polymer matrix will need to be in the lower portion of this range. A typical range of the biologically active agent content for most applicable compounds will be between 0 to 35% by weight. The overall weight of the coating (polymer matrix plus biologically active agent) on the device is typically not important. The weight of the coating attributable to the biologically active agent can be in the range of about 0.1 microgram to about 10,000 micrograms of biologically active agent per $cm^2$ of the gross surface area of the device. More preferably, the weight of the coating attributable to the biologically active agent is between about 1 microgram and about 5000 micrograms of biologically active agent per $cm^2$ of the gross surface area of the device. This quantity of biologically active agent is generally required to provide adequate activity under physiological conditions.

In turn, the coating (polymer matrix plus biologically active agent) thickness of a presently preferred composition will typically be in the range of about 0.03 micrometers to about 100 micrometers. This level of coating thickness is generally required to provide an adequate density of biologically active agent to provide adequate activity under physiological conditions.

As more fully described in the Examples, the cumulative amounts of CVT-313 released from stainless steel plates coated by polymer/biologically active agent composition films with different initial biologically active agent loadings are presented in FIG. 3. All curves exhibit an initial, fast release "burst" fraction, which is released within the first hours, i.e. almost immediately after the device was put into contact with the aqueous medium. This amount of "burst" originates from the fraction of the biologically active agent located on the polymer matrix surface, or from biologically active agent in direct contact with the polymer/medium interface and, therefore, can be released by a convective flow. Obviously, the amount of biologically active agent released in the burst fraction increases proportionally to the initial biologically active agent loading. If it were required that the amount of the biologically active agent delivered in this initial phase be minimized, it would be within the scope of this invention, that the superficially deposited drug fraction (a "burst" fraction) can be removed by washing as one of the steps during the manufacturing of the coated device or before it is adjusted for implantation.

After the surface-deposited biologically active agent was washed out, the biologically active agent release becomes controlled by biologically active agent dissolution and by its diffusion through the polymer matrix. The release rate increases with the increase of the initial biologically active agent loading. For lower loadings, at levels of 10 and 20%, both time dependencies of the released amount follow reasonably closely zero-order kinetics, with release rates almost constant for all the period studied, i.e. up to 60 days. The slopes of the linear fits of data between 8 hrs and 56 days provided the release rates given in Table 4 (Examples).

Still referring to FIG. 3, in the embodiment with the highest loading (25%), two phases, with faster and slower release, can be recognized and approximated by two linear fits. While in the fast phase—lasting for about 12 days—the release rate would be of about 1280 ng/day/$cm^2$, in the second, slower phase, the rate of about 380 ng/day/$cm^2$ was observed, which fits well to the predictable rate/loading dependence, based on the comparison with lower-loading series.

These data illustrate some of the features of the present invention. A thin polymer matrix of a polymer-biologically active agent composition can be created on the metal surface which can efficiently control the release of the biologically active agent through an extended period of time. Using procedures according to the invention, the polymer-biologically active agent matrix can be produced in a reproducible way, that makes it possible to control the release parameters of the biologically active agent. The polymer-biologically active agent polymer matrix is stable and its properties by which the release of the biologically active agent is controlled in a predictable way are maintained for extended time periods.

Additionally, because the polymer binding layer is covalently bound to the metal surface, the polymer matrix is resistant to cracking or peeling. Examples 6 and 14 demonstrate the beneficial effect of the covalent grafting of the underlining binding polymer layer to the metal surface on the stability of the deposited polymer/biologically active agent container layer and its resistance to cracking, fragmentation and detachment from the surface. The superior adhesion, as a result of the covalent binding, provides a durable polymer matrix coating for a medical device, though the device may be subjected to flexion or expansion.

The above description defines the main features of the present invention. The following examples are offered, relating to this invention and the ways it can be carried out, in order that those skilled in the art may more readily understand the present invention and the preferred embodiments thereof. These examples should not to be construed as specifically limiting the invention, and those variations of the invention, which can be developed, now or later, within the purview of one skilled in the art are considered to fall within the scope of the present invention as hereinafter claimed.

EXAMPLES

Example 1

Grafting of Polylactone to Activated Metal Surfaces 1.1. Activation of the metal surface and polymer grafting. Twenty numbered steel plates (316 stainless steel (SS)), 7×7 mm each, were successively washed with hexane, toluene and methanol, treated by a mixture of sulfuric acid and hydrogen peroxide (1:1) for 1 hour at ambient temperature, thoroughly washed by water and dried. The surface of the plates was activated by immersing the plates in a solution consisting of 0.2 ml of (3-aminopropyl)triethoxysilane ("APTES") (available, for example, from Aldrich, Milwaukee, Wis., USA) and 20 ml of acetone and heating under reflux for four hours. Next, the plates were repeatedly washed with acetone and dried in a vacuum at 60° C. The activated plates were transferred into a glass reactor containing crystalline L-lactide (72 mg, 0.5 mmol) (available, for example, from Aldrich, Milwaukee, Wis., USA). The reactor content was flushed with dry nitrogen in repeated nitrogen/vacuum cycles and dried under high vacuum. A solution of anhydrous dioxane (5.0 ml) containing tin(II)-ethylhexanoate (Sn(II)-octoate, 2 mg (0.005 mmol)) was added under inert atmosphere to dissolve the lactide and cover the plates with solution. The solution was maintained at 80° C. for 64 hours to complete the grafting polymerization of lactide on the functional groups of the (aminopropyl)silane-activated surface SS-plates. The plates were removed from the polymerization mixture, washed with hot dioxane and methanol, and vacuum dried to a constant weight.

The presence and the amount of the grafted poly(lactide) layer on the surfaces of plates was determined (a) by measuring the weight gain of plates following the grafting polymerization, and (b) by analyzing the surface chemical composition using ESCA (Electron Spectroscopy for Chemical Analysis).

1.2. Characterization of the grafted polymer layer by measuring the weight gain of the SS plates. Using an analytical electronic microbalance, three values of weights for each plate were determined: W(a)—the weight of a dry plate before silane activation: W(b)—the weight of the dry silane activated plate before polymerization, and W(c)—the weight of the dry plate after polymerization. While the difference between W(a) and W(b) was not found statistically significant, the average weight gain ΔW after polymerization, determined as ΔW=W(c)−W(b), was found as 2.2±0.9 μg/plate. This corresponded to an average thickness of the grafted poly(lactide) layer of 18 nm, assuming a uniform coverage of the surfaces.

In control experiments, matching control plates, i.e., such as plates undergoing the same polymerization reaction without being prior activated by silane reagent, and the silane-activated plates just exposed to the lactide solution without carrying out the polymerization reaction, did not exhibit any significant weight gain.

1.3. Characterization of the grafted binding layer by XPS analysis. The chemical composition of the surfaces of metal plates prepared as in Example 1.1 was analyzed by ESCA using an ESCA 310 (Scienta) apparatus. Typically, the measurements were done in a vacuum of $10^{-9}$ mbar. A monochromatic beam of AlKα (1486.6 eV) was used for electron excitation. The Auger electrons were detected at 10° and 90° angles. The elemental composition of the surface layer was determined from high-resolution spectra and the integrated intensities of respective spectral lines. The various chemical forms of elements found were identified based on comparison of measured binding energies (eV) with corresponding values in NIST database (NIST Standard Reference Database 20, version 1.01, Bickman, D. M. and Wagner, C. D., Gaithersburg, Md. 20899, U.S.A., 1989). In ESCA, the excited electrons originate from a limited depth of the surface layer (of about 7 nm). This depth is dependent on the excitation angle. Therefore, if the composition of the layer varies with the distance from the surface, the elemental composition shown by ESCA will vary with the excitation angle. Thus, from the angle dependence of the elemental composition, the information about the thickness of the modified layer can be obtained.

The characteristic data for the surface composition of plates modified in Example 1.1 are presented in Table 1. Atomal ratios of characteristic elements were obtained at 10° and 90° detection angles. Three series of plates were compared: A: clean SS plates without any modification; B: silane-activated plates; C: silane-activated plates with grafted poly(L-lactide).

TABLE 1

| | % | | | | | |
|---|---|---|---|---|---|---|
| | A | | B | | C | |
| Element | 10° | 90° | 10° | 90° | 10° | 90° |
| Cr | 22.0 | 23.5 | 5.1 | 12.0 | 0.1 | 1.3 |
| Ni | 2.0 | 1.3 | 0.2 | 1.2 | 0 | 0 |
| Fe | 8.6 | 6.0 | 1.7 | 3.8 | 0 | 0 |
| Si | 0 | 0 | 7.3 | 4.6 | 2.8 | 3.0 |
| N | 0 | 0 | 7.5 | 3.4 | 0.6 | 0.6 |
| C | 15.7 | 17.7 | 28.2 | 32.4 | 44.4 | 25.4 |

The first group of elements (Cr, Ni, Fe) is characteristic for the composition of the bare metal surface (316 stainless steel). Some carbon (and oxygen) is regularly present on the surfaces of untreated metal as an impurity. Si and N (in addition to carbon) are characteristic elements of the siloxane activating layer as follows from their presence at surfaces of series B and C. The decreased content of Cr and other metals at the surfaces of series B and C confirms the modification of the surface by silane activation and, in particular, coverage of the metal by grafting of lactide. In series B, the higher content of Si for low incident angle (10°) indicates that the most superficial layer is richer in Si with respect to the deeper layers, which correspondingly show higher content of Cr and other metals. Practically complete disappearance of electrons originating from Cr and other metal elements in series C, confirms a complete coverage of the metal by the grafted polymer, and makes it possible to estimate a minimum thickness of grafted PLLA layer as being higher than about 10 nm, which corresponds with the thickness of the grafted layer estimated by weighing (Example 1.2). The presence of a significant layer of PLA is also confirmed by the increased content of carbon and its angle dependence.

The analysis of the binding energy of emitted electrons provides the information about the chemical forms in which the elements are present in the surface layer, thus makes it possible to confirm the anticipated chemical processes. The characteristic data showing the changes in the composition of characteristic chemical groupings after grafting of lactide to the silane-activated metal surface as in Example 1.1 are presented in Table 2. B: silane-activated plates (APTES); C: silane-activated plates with grafted poly(L-lactide).

TABLE 2

| Element | Chemical form (binding energy, eV) | % B | % C |
|---|---|---|---|
| C | $CH_x$ (284.5 eV) | 33.3 | 29.2 |
|   | C—O (286.1 eV) | 6.9 | 10.3 |
|   | C=O (288.0 eV) | 4.5 | 6.0 |
| O | C=O (531.3 eV) | 21.4 | 37.3 |
| N | —$NH_2$ (399.5 eV) | 3.7 | 0 |
|   | —NH— (400.4 eV) | 0 | 2.7 |

The covalent grafting involving the acylation of functional groups present in the (aminopropyl)silane-activated layer is confirmed by the changes of characteristic chemical structures. At the (aminopropyl)silane-activated surfaces nitrogen (N, 1s) is present in a form of amine. After grafting with lactide, the acylation of the amine groups and formation of amide is confirmed by the change of binding energy of nitrogen electrons to that characteristic for amide. Correspondingly, the formation of the polyester structure is indicated by the increase in the content of carbonyl groups.

The presence of initiating amine groups on the silane-activated surface was also documented by analyzing the mole amount of amine groups on the activated suraface as follows. The plates were immersed in a 0.1% solution of 2,4,6-trinitrobenzenesulfonic acid in 3% borate buffer (pH 8.15) for 5 minutes at 70° C. Then, the plates were thoroughly rinsed with water to remove the unbound reactants and treated with a solution of NaOH (1 mol/L) at 70° C. for 10 minutes. The amount of liberated picric acid was determined by reverse phase HPLC chromatography. The content of amino groups determined by this procedure on different batches of activated SS plates prepared by the procedure described in this Example was typically in the range of 0.4 to 1.5 nmol/$cm^2$.

1.4. Deposition of the container polymer layer. To evaluate the effect of the grafting (or binding) layer on the properties of polymer coating composition, controlled experiments with well-defined coating procedures were performed. Additional layers of polymers were deposited on the polymer-grafted plates by using a spin-coating process. In general, a solution of the polymer in a solvent was applied on one surface of the plate and spread over it by spinning the plate in the spin-coating apparatus (Headway Instruments). After evaporation of the solvent and vacuum drying, the amount of deposited polymer was determined by weighing. The surface profile of the polymer layer was analyzed by means of a surface profiler (Surface Profiler Tencor, model AlfaStep500). The thickness of the deposited polymer (or container) layer could be well controlled by the concentration of the applied polymer solution and by the frequency of spinning. Additionally, several subsequent layers of the polymer could be deposited on the top of previous one by applying the same procedure. This procedure made it possible to form well-defined polymer layers in a reproducible way on grafted and non-grafted plates.

Poly(L-lactide) (PLLA, $M_w$=365,000) was deposited using the above described procedure as a solution in dioxan (2% w/w) on the surfaces of three series of SS plates (n=5 each) prepared as in Example 1.1: series D: clean SS plates without any modification; series E: silane-activated plates without further modification; series F: silane-activated plates with grafted poly(L-lactide). Four successive layers of poly(L-lactide) were deposited in each series. The average deposited amounts and thickness of the polymer layer are shown in Table 3.

TABLE 3

| Series | Layer 1st | 2nd | 3rd | 4th | Total (μg) | Thickness (μm) |
|---|---|---|---|---|---|---|
| D | 34.4 ± 2.3 | 64.4 ± 3.4 | 97.2 ± 5.3 | 105.6 ± 5.4 | 301.6 ± 6.8 | 5.03 ± 0.11 |
| E | 42.2 ± 2.7 | 70.8 ± 3.1 | 92.8 ± 4.1 | 103.2 ± 5.2 | 309.0 ± 4.8 | 5.15 ± 0.08 |
| F | 55.8 ± 4.2 | 75 ± 3.9 | 105.8 ± 14.6 | 109.6 ± 6.7 | 346.2 ± 12.7 | 5.77 ± 0.21 |

The data in Table 3 show that the thickness of the newly deposited polymer layer depends on the properties of the underlying surface. The increase in the amount of the polymer deposited in the second and third layers reflects the improved adhesion of the polymer to the underlying surface because the deposition is done on the layer of the same polymer deposited previously. In addition, when the second and any subsequent layers are deposited, the solvent of the applied solution partly penetrates into the underlying polymer, leaving the spreading solution more viscous, thus increasing the thickness of the spread layer. While the differences in these effects become negligible for third and any subsequent layers, the differences between series D, E and F in the amount deposited in the first layer reflect their differences in the surface properties. The significantly higher amount of the polymer deposited in the series F, compared to series D and E, reflects the higher adhesion of the deposited polymer to the underlying covalently grafted polymer binding layer as well as solvent penetration into it.

The deposited polymer layer (or container layer) can be dissolved in a suitable solvent and completely washed down from the plates. In the above described experiment, the series of plates containing the deposited PLLA layers were thoroughly washed with chloroform, which is a good solvent for PLLA. In the series F plates, the covalently grafted polylactide layer remained on the surface of the plate even after extensive washing of the deposited PLLA layer (a container layer), and its persistent presence on the metal surface was proved by both the XPS analysis and surface-profile methods as described above. In the series E and D, the washing of deposited PLLA (a container layer) caused a complete removal of deposited PLLA and their surface characteristics, as determined by the above methods, indicated a silanized and bare metal-oxide surfaces in the series (E) and (D), respectively.

These experiments show that the grafting procedure according to this invention produces a covalently bonded polymer layer (a binding layer) on the metal surface. The binding layer is resistant to removal by dissolution in a good solvent for the polymer. The covalently grafted binding layer improves the adhesion of the adjacent layer (layers) of a compatible polymer, deposited on top of it (as the container layer).

Example 2

Surface Activation with APTES in Vapor Phase

SS plates, similar to those in Example 1.1, were rinsed with toluene, methanol and distilled water, blown dry with stream of nitrogen and placed in a vacuum chamber of a radio frequency glow discharge (RFGD) plasma generator (Model 220RGD-200, REFLEX Analytical Corp. Ridgewood, N.J.). Plates were treated with argon plasma for 3 to 5 min (80 to 100 W, 1 to 10 mbar). Surfaces prepared with this procedure showed no organic contamination by ESCA analysis. The freshly plasma-cleaned plates were placed in a glass container, where they were fixed in a PTFE holder which kept their flat surfaces facing the liquid at the bottom of the container. The container was flushed with nitrogen saturated with water vapors and 0.5 ml of APTES was dropped at the bottom under the nitrogen shield. The plates were exposed to APTES vapors for intervals of from 10 minutes to 16 hours. After exposure to silane vapors the plates were removed from the container, purged with nitrogen, evacuated and heated in a vacuum oven to 60° C. for 2 hours to remove residual physically adsorbed silane reactant.

The amine functional groups on the activated surface were determined as follows. The plates were immersed in a solution of 2,4,6-tri-nitrobenzenesulphonic acid in 3% borate buffer (pH 8.15) for 5 minutes at 70° C. Then, the plates were thoroughly rinsed with water to remove the unbound reactants and treated with a solution of NaOH (1 $molL^{-1}$) at 70° C. for 10 minutes. The amount of liberated picric acid was determined by a reversed phase HPLC chromatography. The content of amino groups was found to be 0.6, 0.9 and 1.2 $nmol/cm^2$, for plates treated with SAR for 10, 30 and 60 min, respectively. The content of amine groups on the surface reached saturation after 60 minutes of exposure.

The activated plates were grafted by in situ polymerization of L-lactide in dioxane by the procedure described in Example 1.1. The grafting efficiency, estimated from the ESCA analysis and the thickness of the grafted layer was essentially the same as that described in Example 1.1.

Example 3

Bis-N-(2-hydroxyethyl)aminopropyl triethoxysilane as a Silane Activating Reagent Bis-N-(2-hydroxyethyl)aminopropyl triethoxysilane was used instead of APTES as a silane activating reagent (SAR) in a manner described in Example 1.1. By carrying out the grafting polymerization according to Example 1, metal surfaces containing an average amount of 2.6±0.8 $ug/cm^2$ of covalently bound polylactide were obtained. The plates were further used for deposition of the container polymer layer as it was described in Example 1.4.

Example 4

Grafting of poly(D,L-lactide) to APTES Activated Metal Surface 10 pieces of SS plates analogous to those described in Example 1, were activated by the reaction with APTES as in Example 1, to provide metal surfaces with the average content of amine groups 0.8 $nmol/cm^2$. The activated plates were placed in a glass ampule and 2.9 grams of crystalline D,L-lactide (m.p. 125° C.) and 40 mg of tin(II)octanoate were added. The ampule was flushed by dry nitrogen using repeated vacuum/nitrogen cycles, kept at 60° C. under a high vacuum for 2 hours and sealed under vacuum. The sealed ampule was heated in an oil bath to 180° C. in order to melt the lactone. While taking care that all plates were immersed in the lactone melt, the reaction was kept at 180° C. for 24 hours. During this period, the lactone melt became viscous. When taken our of the heated bath, the lactone melt solidified to a glassy solid. The solid polymer was dissolved in chloroform, the plates were removed and repeatedly washed with hot dichloroethane and dried in stream of nitrogen and vacuum. The presence of poly(D,L-lactide) (PDLLA) grafted to the metal, i.e. the polymer remaining on the surface after thorough washing with the solvent, was confirmed by the methods described Example 1. The average thickness of the grafted polylactide layer was estimated to be about 20 nm. The PDLLA-grafted plates were suitable for deposition of a polymer coating layer (container layer) in a similar way as it was described in Example 1.

Example 5

Release of Biologically Active Agent from Coated Metal Surface

SS plates (7.1×7.1 mm, surface area ~50 $mm^2$) analogous to those described in Example 1, were activated by the reaction with APTES and grafted by polymerization of lactide, as in Example 1.1, to provide a PLA binding layer on the metal surfaces with an average content of grafted PLA of 3.5 $micrograms/cm^2$.

Additional PLA layers (container layers) containing a biologically active agent were applied to the grafted plates. The polymer-biologically active agent layers were cast on one side of each SS-plate by applying a dioxane solution of PLA and the biologically active agent and spreading it on the surface of the plate by spinning it in a spin-coater device (Headway Instruments). The solvent was evaporated from the spread layer of the polymer solution to solidify the polymer film (as a container layer). Another layer of the polymer-biologically active agent composition was applied in the same way (to form another sublayer of the container layer), when the previous one was fully dried. The average thickness of the container layer was determined by weighing. The actual average biologically active agent loading for any given sequence of polymer-biologically active agent film deposition was determined by dissolution of films from a control series of plates and measuring the biologically active agent content in the recovered solution.

The PLA polymer used was poly(D,L-lactide), (PDLLA, MW=800,000) and its concentration in the dioxane solution was 18 mg/ml. The biologically active agent, CVT313, is a purine derivative, which has been shown as a CDK2 inhibitor (Brooks, E. E., et al., *J Biol. Chem* 1997, 272, 29207).

Three series, G, H and J, of coated plates were prepared by applying the solutions containing the same concentration of PDLLA and the biologically active agent in the concentration of 2, 4, and 6 mg/ml, respectively. The PDLLA-CVT313 container layers were produced by applying two subsequent sublayers for each plate, thus providing for coatings with an average thickness of 2.9 micrometers and with average contents of CVT313 in the polymer matrix of series G, H and J being 10.3, 18.9 and 25.1% (w/w), respectively.

The one-side-coated SS-plates were suspended in a buffered saline solution of pH 7.4 in a stoppered spectrophotometer cell with the coated surface exposed to the solution. The cell was placed in a metal holder allowing the buffer to be stirred in a constant rate by means of a magnetic stirrer and to keep the temperature constant at 37° C. The incubation of the plates carrying the polymer-biologically active agent polymer matrix was carried out for two months. In this time period, the concentration of the biologically active agent released to the buffer was determined by measurement of UV-absorption spectra of the solution. The amount of released biologically active agent was determined from the biologically active agent concentration and the volume of the recipient solution and plotted against time of incubation. The daily release rate was calculated from linear portions of the release profiles. The cumulative amounts of CVT313 released from the three series of plates coated by polymer-biologically active agent polymer matrix films with different initial biologically active agent loadings are presented in FIG. 3. The average values of triplicate release data are plotted against linear time scale.

After 60 days, the plates were removed from the buffer, rinsed by water and dried under vacuum. The content of the residual agent in the polymer coating was determined by dissolution of the coating in chloroform and measuring the content of the agent in the solution by HPLC. A summary of the quantitative data is given in Table 4.

TABLE 4

| Parameters of the release system (units) | G | H | J |
|---|---|---|---|
| Film thickness (μm) | 2.88 | 2.85 | 3.02 |
| Initial loading of the biologically active agent in the matrix (%) | 10.3 | 18.9 | 25.1 |
| Fraction released during 60 days (%) | 46 | 41 | 40 |
| Fraction remaining in the matrix (%) | 53 | 56 | 57 |
| Initial-burst fraction (%) | 5.4 | 8.6 | 10.5 |
| Release rate [a] (ng/day/cm$^2$) | 200 | 320 | 1280 [b] |
| | | | 380 [c] |

Figure 3:
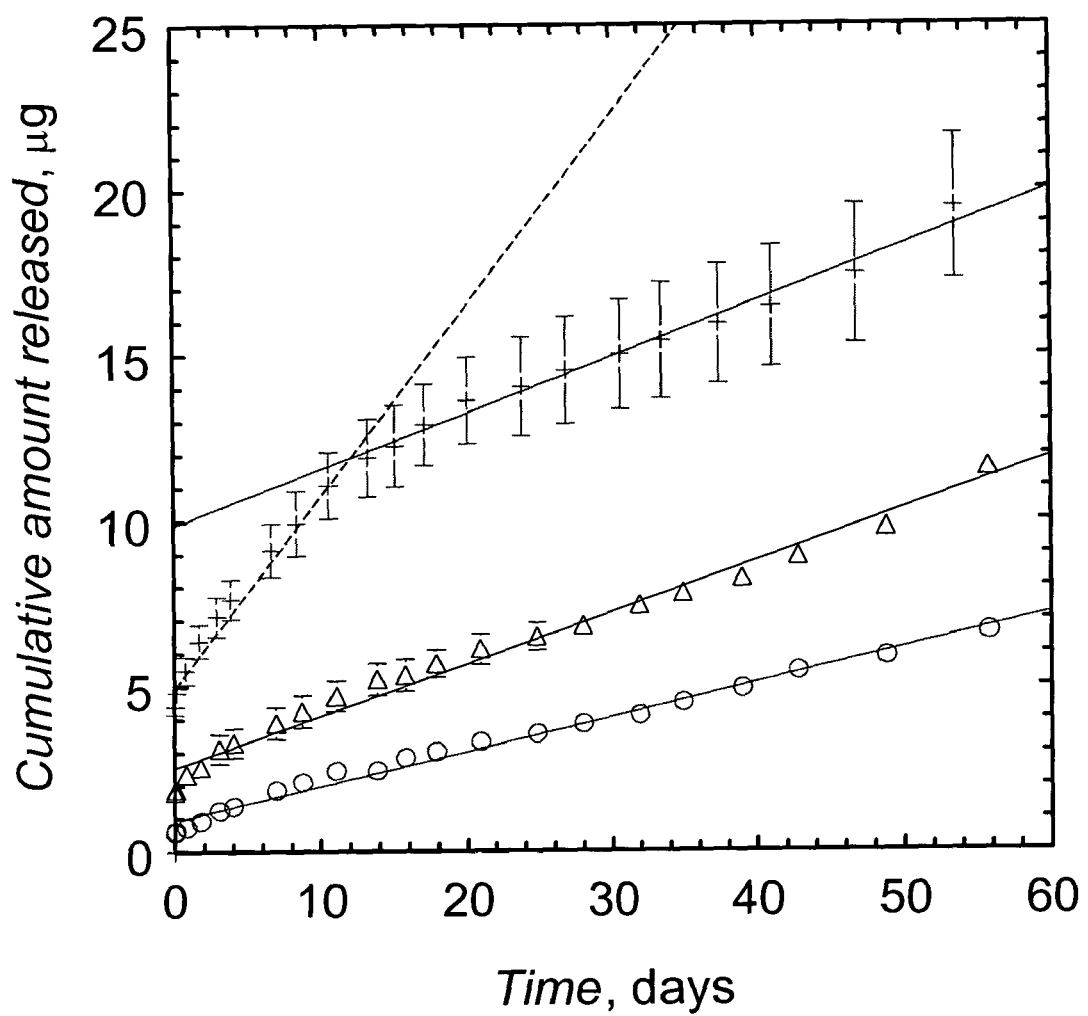
FIG. 3 is a graph showing the release of a biologically active agent from a coated metal surface of the present invention. The cumulative amount (in mg) of CVT-313 released from PDLLA films to PBS plotted against time (days) for different initial concentrations (w/w) of CVT-313 in the film (n=3): o—series G (initial conc 10.3%); Δ—series H (initial conc 18.9%); +—series J (initial conc 25.1%).

[a] extrapolated from the linear fit of the released amount vs. time dependences;
[b] based on the initial fast-release phase (see FIG. 3);
[c] based on the second slow-release phase (see FIG. 3).

Example 6

The Effect of Coating Stability on the Release of Biologically Active Agent

Three series of SS-plates (n=6, each), analogous to those of Example 1, were prepared. Series K consisted of plates activated by the reaction with APTES and subsequently grafted by in situ polymerization of poly(D,L-lactide), using the procedure described in Example 1. Series L consisted of plates activated by reaction with APTES as a silane-activating agent only. The series M was composed of bare cleaned SS-plates without further modification.

A container layer of the same PDLLA/CVT313 polymer/biologically active agent solution was deposited by spin casting from a dioxane solution on one side of plates of all three series K, L, and M, using the procedure described in Example 5. The average thickness of the deposited coatings was 3.1±0.2 micrometers, and the average content of CVT313 in the deposited container layer was 11.4±0.3% (w/w) for all three series. The plates were individually immersed in a phosphate buffered saline solution (PBS, pH 7.4) and the release of the biologically active agent from each plate was followed as described in Example 5.

In series K (polymer/biologically active agent solution deposited on PLA grafted surface), release profiles closely corresponding to those shown for series H of Example 5 were observed for all plates in the series (n=6). The average release rate in the period between $1^{st}$ and $12^{th}$ days was found to be 208±12 ng/day/cm$^2$. The average fraction of the biologically active agent remaining in the polymer matrix after 12 days of the release experiment was 78±6% of the original loading. Inspection of the container layer under the optical microscope showed unperturbed uniform polymer matrix over all of the plate surface.

In series L (polymer/biologically active agent composition deposited on SS modified by silane activation only), the release profiles showed a rapid increase in the release rate starting from the second day of the release experiment in some plates. Within four days, the fraction of the biologically active agent released to the medium approached 100% for all plates in the series. The inspection of the container layer under the microscope showed a progressive cracking of the container layer starting on the second day of the experiment, followed by peeling of fragments of the polymer film from the surface.

In series M (polymer/biologically active agent composition deposited directly on the bare metal surface), the release profiles were analogous to those of series L. The disturbances in the release rate due to fragmentation of the container layer and its peeling from the metal surface started within 24 hours after the plates were immersed in PBS. The visual inspection under microscope confirmed insufficient adhesion of the deposited polymer/biologically active agent film to the surface.

Example 7

Release of Biologically Active Agent from Coating with PDLLA Skin

Two series of SS-plates, N and P, were treated by silane activation reagent and grafted by in situ polymerization of lactide, applying the procedures described in Example 1. In both series, one side of the plates with a surface area of 50 mm$^2$ was coated (container layer formed) by polymer/biologically active agent composition composed of poly(L-lactide) (PLLA) and CVT313, which was applied in two sublayers as a solution in chloroform using the spin-coating method. The average film thickness PLLA/CVT313 composition was 2.74±0.16 micrometers and the average content of CVT313 in the film was 28.8±1.2% (w/w). In series N (n=4), an additional coating layer of pure PDLLA (a "skin", void of the agent) was applied on the top of the PLLA/CVT313 film. The plates of series P (n=4) were used without any additional modification.

Figure 4:
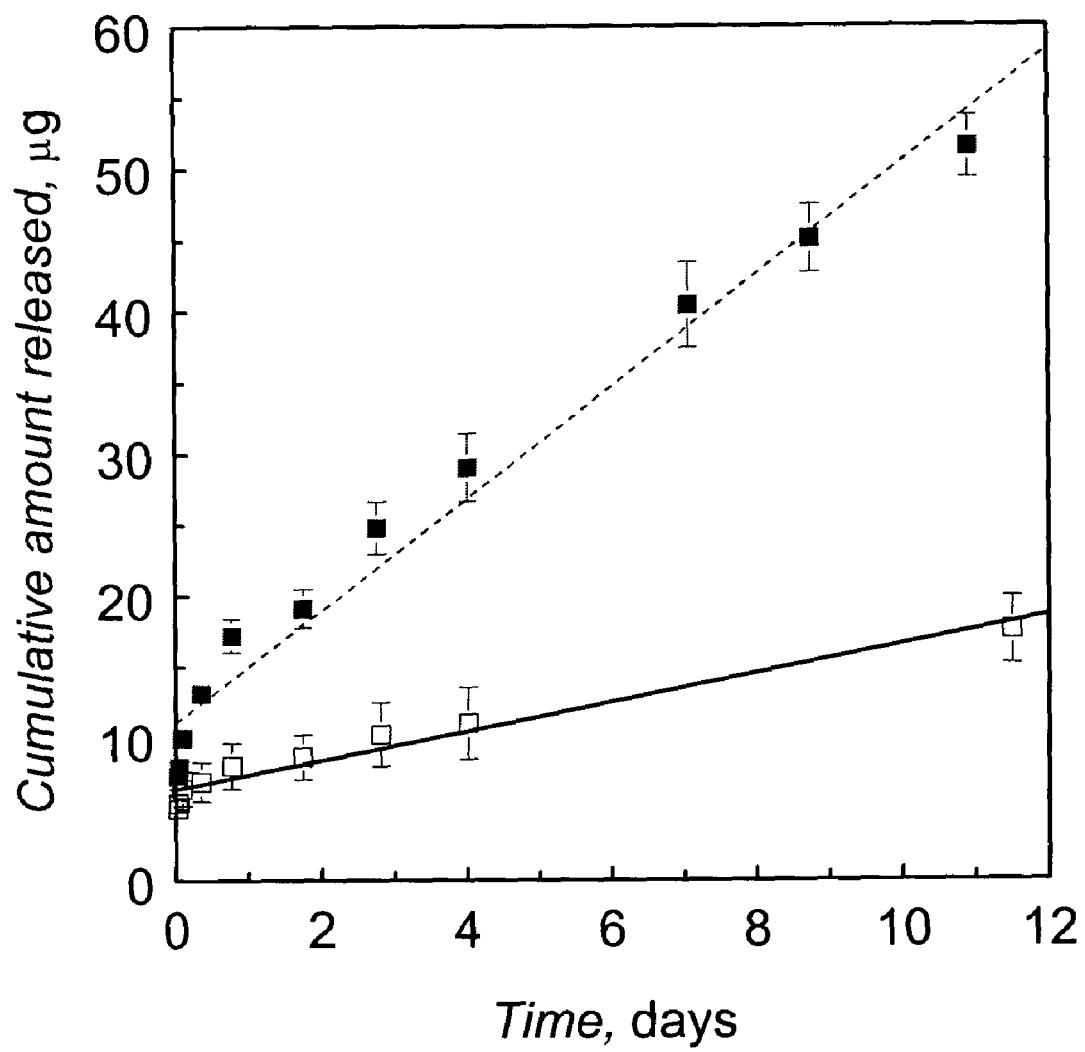
FIG. 4 is a graph showing the release of a biologically active agent from a coated metal surface of the present invention. Comparison of the release from plates of series N (open points) and P (filled points) showing the effect of PDLLA skin layer on the release of CVT313 from the same container matrix (PLLA) (n=4).

The plates of both series were immersed in a stirred PBS solution and the release of biologically active agent to the solution was monitored. The time profiles of the release of CVT313 from PLLA matrix and PLAA matrix with PDLLA "skin" are shown in FIG. 4. The release parameters of both systems are summarized in Table 5.

TABLE 5

| Parameters of the release system [a] (units) | N (PLAA + PDLLA skin) | P (PLLA) |
|---|---|---|
| Film thickness (μm) | 3.06[b] | 2.74 |
| Initial loading of the biologically active agent in the matrix (%) | 24.6 [c] | 28.8 |
| Fraction released during 12 days (%) | 42.5 | 93.4 |
| Fraction remaining in the matrix (%) | 62.4 | 13.4 |
| Initial-burst fraction (%) | 15.2 | 20.6 |
| Release rate (ng/day/cm$^2$) | 2040 | 8300 |

[a] average values, n = 4
[b] composed of 2.74 μm of PLLA/CVT313 matrix and 0.32 μm PDLLA skin
[c] including the skin layer in the calculation Example 8

Release of Biologically Active Agent from Coating of Bone Fixation Plates

Bone-fixation plates (stainless steel, 7×49 mm) were activated by the reaction with APTES and subsequently grafted by in situ polymerization of D,L-lactide according to Example 4.

The grafted plates were coated by a poly(D,L-lactide)/dexamethasone composition by a dip-coating procedure as follows. The plate, hung on a wire holder through a hole in the plate, was immersed in a solution of PDLLA and dexamethasone in chloroform for about 10–15 seconds, and removed from the solution in a vertical position. The excess of the solution collected at the bottom end of the plate was dried by touching with paper tissue. The plate wetted by the composite solution was then placed flat on a support holding it in a horizontal position and dried. The drying took place at room temperature under a stream of nitrogen (2 hours), followed by drying in a vacuum oven at 50° C. (16 hours). By evaporation of the solvent, a contiguous layer of polymer/biologically active agent film was formed. The amount of deposited polymer/biologically active agent composition was determined by weighing.

Using the above procedure, two series of plates were prepared. The polymer used was poly(D,L-lactide) (PDLLA, MW=800 000). The agent was dexamethasone (Sigma, Cat. No.:D1756). The composition of PDLLA/dexamethasone solutions in chloroform used for dip coating was: series A (n=3): PDLLA, 17.05 mg/ml, dexamethasone 4.15 mg/ml; series B (n=3): PDLLA, 18.05 mg/ml, dexamethasone, 2.64 mg/ml. The average thickness of the film in both series was about 1.6 μm (estimated from the weight of the coating and the surface area of the plates). Based on the composition of the coating solution, the initial biologically active agent loading was 19.6% w/w and 12.8% w/w for the series A and B, respectively.

The release of dexamethasone from plates in a simulated body fluid (buffered isotonic saline solution with bovine serum albumin) was followed at 37° C. for 12 days. The amount of released dexamethasone was determined by HPLC in the samples withdrawn from the incubation solution at selected time intervals. The obtained release profiles, expressed as a cumulative fraction of biologically active agent released with time, are given in FIG. 5.

Figure 5:
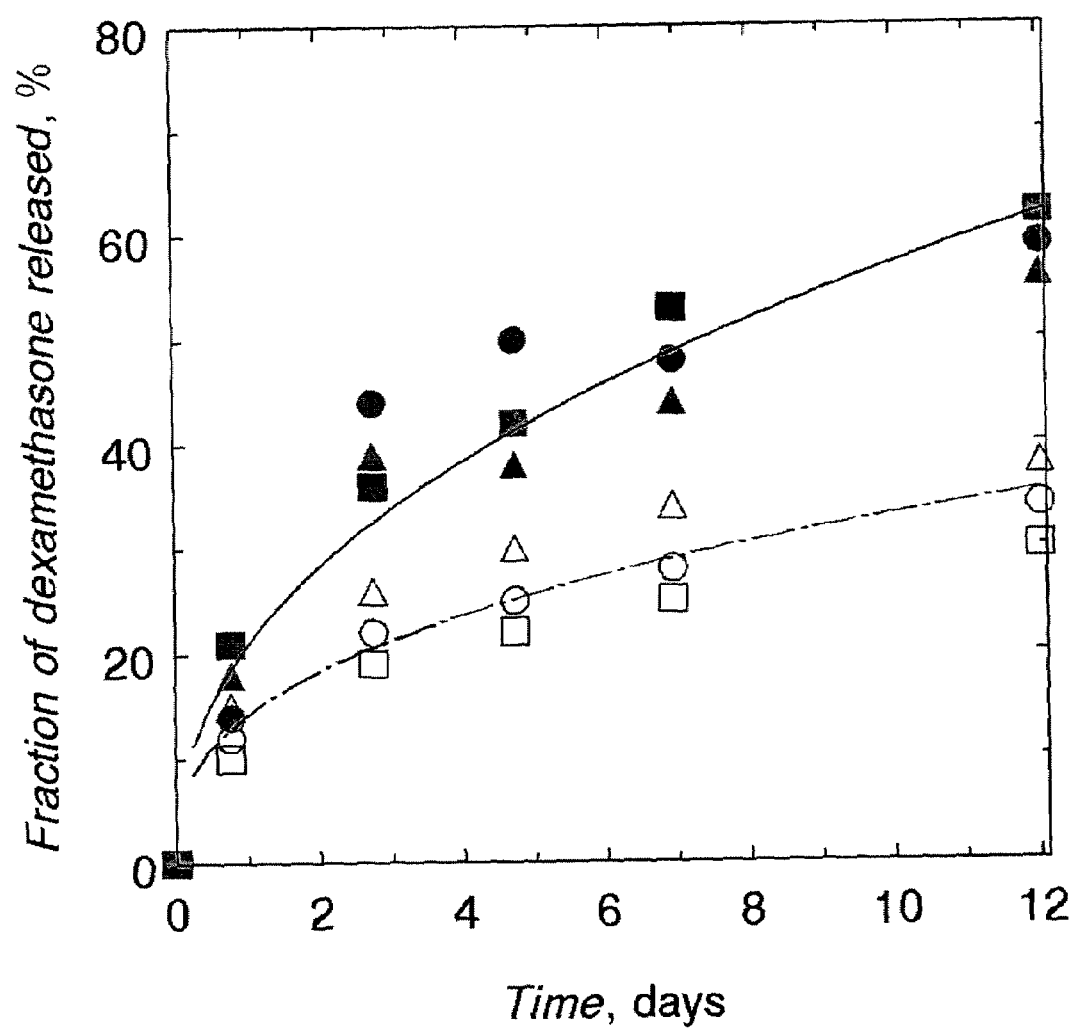
FIG. 5 is a graph showing the controlled release of dexamethasone from PDLLA coated stainless steel plates for PDLLA/dexamethasone composition with different dexamethasone loading: series A (n=3), 19.6% w/w (filled points); series B (n=3) 12.8% w/w (open points).

The data in FIG. 5 demonstrate that the polymer coating composition was provided with the capacity to control the release of incorporated anti-inflammatory drug, dexamethasone, for an extended time period and to deliver the drug in a predictable fashion to the surrounding environment, such as simulated body fluid. The release rate and, therefore, the daily delivered dose, of the drug was dependent on the drug loading in the composition.

Example 9

Release of Biologically Active Agent from Coated Coronary Stents

A series (n=5) of balloon expandable coronary stents (stainless steel, 3×16 mm) (Pulse Corporation) may be surface activated (to form an activating layer) and grafted (to form a binding layer) by the in situ polymerization of D,L-lactide using the procedure described in Example 2. The grafted stents may be coated by a composition consisting of 78% of poly(lactide-co-glycolide) copolymer (lactide/glycolide ratio: 15/85) and 22% of warfarin sodium (an anticoagulant drug, MW 330) (to form a container layer), by applying the mixture of both components as a solution in hexafluoropropanol (HFP) by dipping the stent in the solution. The polymer/biologically active agent film should be solidified by evaporating the solvent in vacuum. After complete removal of HFP, an additional coating layer (a barrier or skin layer) of poly(D,L-lactide) can be applied from the solution of PDLLA in acetone as described in Example 7.

The release of warfarin from the coated stents in simulated blood plasma (buffered isotonic saline solution with bovine serum albumin) can be followed as described in Examples 5 through 8. The amount of released warfarin may be determined by a reverse-phase HPLC in 24 hours intervals. Based on the analysis of the release profiles, the coated coronary stents thus produced should provide for a sustained release of the anticoagulant agent in the dose of 0.85 μg/day/stent for the period of more than 8 days, which dose could be administered locally to the implantation site. The release of anticoagulant agent thus can improve the performance of the stent after its implantation.

Example 10

Release of Biologically Active Agent from Coated Mandibular Implant

A titanium mandibular implant may be treated by oxygen RFGD plasma and subsequently surface activated by the reaction with bis-N-(2-hydroxyethyl)aminopropyl triethoxysilane in a vapor phase (to form the activating layer). The activated surface may be grafted (to form the binding layer) by the in situ polymerization of ε-caprolactone in THF, with tin(II)-ethylhexanoate as a catalyst. The thickness of the resulting grafted (binding) layer can be determined by means of a surface profiler (Tencor, model AlfaStep500) and is expected to be in the range of 10 to 30 nm. The grafted implant can be coated (to form a container layer) by a composition, consisting of 74% of poly(caprolactone) (MW 80000) and 26% of mitomycin, as a solution in chloroform, by spraying the solution on the implant in layers. Each sprayed sublayer of solution should be dried in a stream of hot nitrogen before another layer iss applied. The top most layer (barrier or skin layer) may be applied from a solution of poly(caprolactone) only, without the biologically active agent. The average thickness of the composite coating (polymer matrix plug biologically active agent) on the implant surface is expected to be in the range of 15 to 20 μm. Thus, a medical implant, releasing a dose of 180 μg/day/cm$^2$ of an antiproliferative and antimicrobial agent in a sustained way, can be produced.

Example 11

The Release of CVT313 from Coated Coronary Stents

A series (n=3) of balloon expandable coronary stents (stainless steel, 16 mm) (Pulse Corporation) were surface activated by the reaction with APTES and grafted (binding layer) by the in situ polymerization of L-lactide using the procedure described in Example 1. The grafted stents were coated (container layer) by a composition consisting of poly(D,L-lactide) (PDLLA, Mw=625,000) and a biologically active agent. The agent, CVT313, is a purine derivative, which has been shown as a CDK2 inhibitor (Brooks, E. E., et al., J. Biol. Chem 1997, 272, 29207).

The coating (container layer) of stents was accomplished by spraying a solution of PDLLA (56.0 mg) and CVT313 (4.35 mg) in dioxane (8.60 ml) on the spinning stent, using a microspray device with nitrogen as a carrier gas. The solvent was left to evaporate at room temperature and finally dried under vacuum. A uniform, contiguous, and smooth coating (container) layer on all surfaces of the stent struts was obtained with average thickness of about 1.1 μm. The average total weight of the coating layer on the stent was 65.9±2.2 μg and the average content of the active agent in the coating composition (container layer) was 7.2% w/w.

Figure 6:
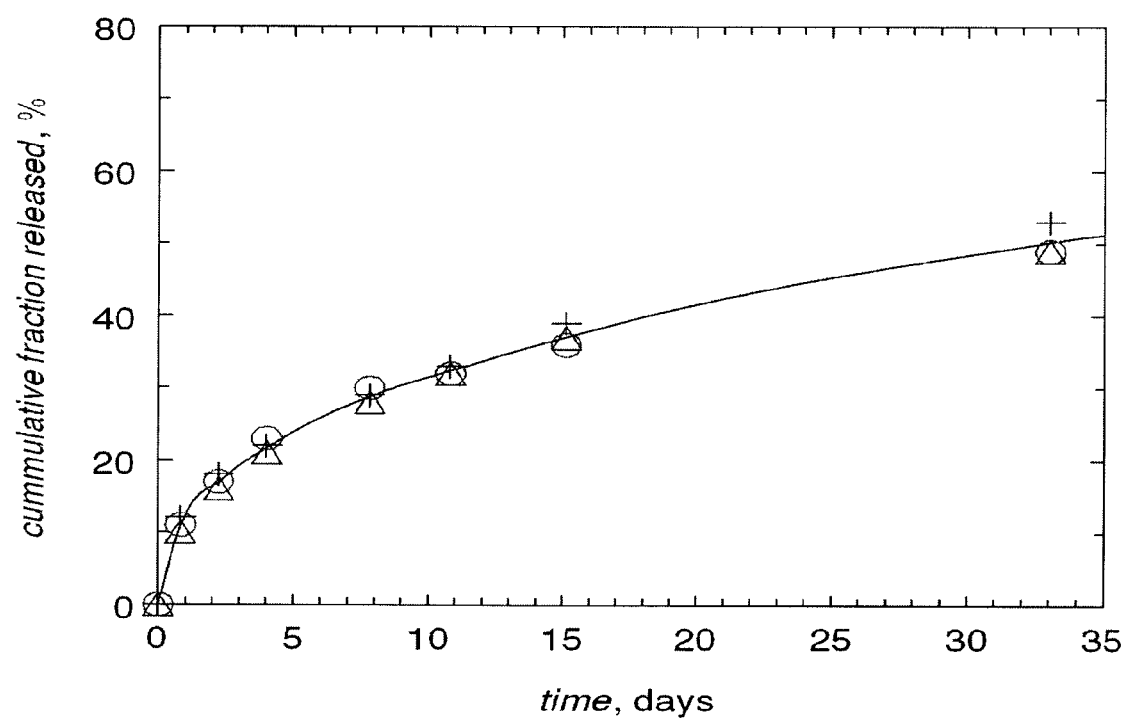
FIG. 6 is graph showing the release rate profile of CVT313 from coated coronary stents of the present invention. The symbols show the measured values for individual stents (n=3). The line represents the average values.
Figure 7:
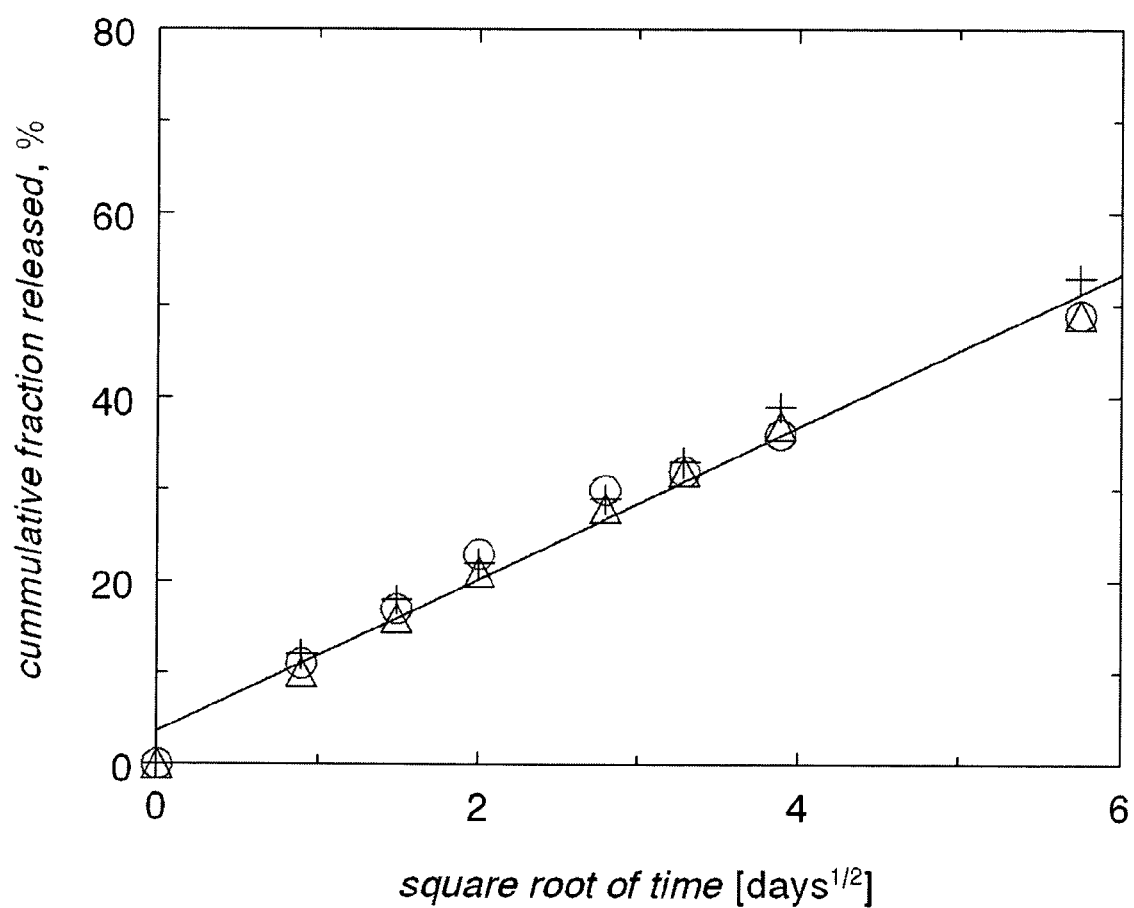
FIG. 7 is a graph showing the release rate for the same data shown in FIG. 6 on a square-root of time scale. The cumulative amount of released CVT313 from coated coronary stents in % of total loading plotted on a square-root-of-time scale. The symbols show the measured values for individual stents (n=3). The line represents the linear fit. The linear dependence of the released amount on the square-root of time indicates the compliance with the diffusion controlled mechanism of release, typical for the monolithic matrix devices. Higuchi, T., Rate of release of medicaments from ointment bases containing drugs in suspensions. *J. Pharm. Sci.*, 50: 874–875 (1961); Higuchi, T., Mechanism of sustained-action medication, theoretical analysis of rate of release of solid drugs dispersed in solid matrices. *J. Pharm. Sci.*, 52: 1145–1149 (1963).

The release of CVT313 from the coated stents in phosphate buffered isotonic saline was followed under constant stirring rate of the solution at 37° C., for 35 days. The amount of released agent (CVT313) was determined by HPLC. Based on the analysis of the release profiles, the coated coronary stents thus produced provided for a sustained release of CDK2 inhibitor for a period of more than 35 days. During the period between day 1 and day 35, the release profile was almost linear with an average dose of released CVT313 being 72 ng/day/stent. During this period about 51% of the incorporated agent was released. The analysis of the residual amount in the coating matrix gave 48% of the original amount of agent still residing intact in the coating matrix. Taking into account the residual amount of agent and the average rate of release on day 35, when the experiment was terminated, one can extrapolate the capacity of the device to release the agent for a total of about 70 days. The release profile and the variation in the release rate between individual stents in the series is shown in FIGS. 6 and 7.

Example 12

The Release of Bioactive Agent from Semicrystalline and Amorphous Matrices

SS plates (7.1×7.1 mm, surface area ~50 mm2) analogous to those described in Example 1, were activated by the reaction with APTES and grafted by polymerization of lactide, as in Example 1.1. A PLA polymer container layer containing a biologically active agent was applied onto the grafted lactide layer by spin casting from a polymer-agent solution.

The polymers used for the container layers were
(a) poly(D,L-lactide), (PDLLA, MW=800,000),
(b) poly(L-lactide), (PLLA, MW=365 000) and
(c) a copolymer of L-lactide and D,L-lactide, poly(L-lactide-co-D,L-lactide), prepared from L-lactide and D,L-lactide monomers in the ratio of 1:1, (P-LL-co-DL, MW=350 000), L-lactide/D-lactide structural units ration in the copolymer=0.75)

Five series of SS plates, designated as series Q, R, S, T, and U, coated by the above polymers as follows. In series Q the polymer of container layer was PLLA; in series R the container layer was cast from the mixture of PLLA and PDLLA in the ratio of 3:1 (w/w); in series S the container layer was composed of a PLLA and PDLLA mixture in the ratio of 1:1; in series T the container layer was cast from the solution of copolymer P-LL-co-DL (1:1); and in series U the container layer was composed of PDLLA. Consequently, the approximate composition of polymer forming the container layer in series Q, R, S, T, and U with respect to the ratio of L-lactide and D-lactide structural units was expected to be as follows:

| Series | L-Lactide/D-lactide ratio |
| --- | --- |
| Q | 1.00 |
| R | 0.88 |
| S | 0.75 |
| T | 0.75 |
| U | 0.50 |

In all series the container layer was cast from the solution of polymer, or mixture of polymers, and the agent in dioxane. The concentration of polymers in the dioxane solutions was 16 mg/ml.

The agent used in all series was CVT313, a purine derivative, known as a CDK2 inhibitor (Brooks, E. E., et al., J Biol. Chem 1997, 272, 29207). The average content of the agent in the container layer was the same for all series and was equal to 172±7 ug/mg of polymer-agent composition, i.e. the loading degree of 17% (w/w).

Figure 8:
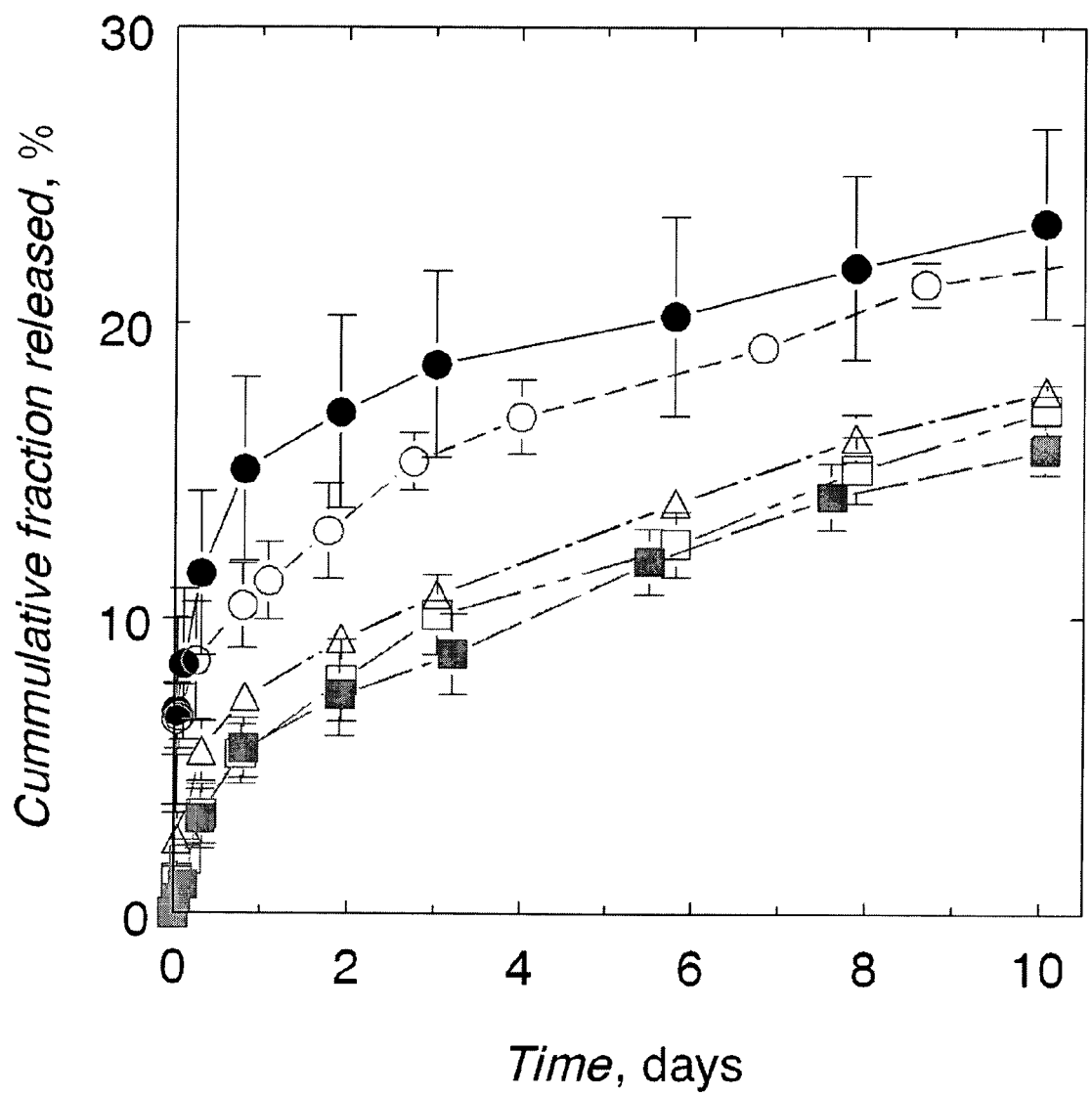
FIG. 8 is a graph showing the release rate profile for CVT313 from coated metal surfaces of the present invention. The fraction of CVT 313 released over 10 days period from the series of coating films formed by polylactide compositions with different ratio of L-lactide and D-lactide structural units. Series Q (filled circles): PLLA (L-LA/D-LA=1.00); series R (open circles): PLLA/PDLLA 3:1 blend (L-LA/D-LA=0.88); series S (triangles): PLLA/PDLLA 1:1 blend (L-LA/D-LA=0.75); series T (open squares): P-LL-co-DL (L-LA/D-LA=0.75); and series U (filled squares): PDLLA (L-LA/D-LA=0.5).

The one-side-coated SS-plates were suspended in a buffered saline solution of pH 7.4 in a stoppered spectrophotometer cell with the coated surface exposed to the solution and the amounts of the agent released from the coatings were determined by measurement of UV-absorption spectra of the solution. The amount of released agent was determined from the agent concentration and the volume of the recipient solution and plotted against time of incubation. The cumulative fractions of CVT313 released from the five series of plates coated by polymer-agent composition films with same content of the agent and different ratio of L-lactide and D-lactide structural units in the polymer matrix are presented in FIG. 8. The average values of triplicate release data are plotted against a linear time scale.

The release data for the series of polylactide compositions with different ratio of d-lactide and L-lactide structural units in the matrix demonstrate that the release profile, i.e. the release rate and the fraction released in the fast initial phase, depends on the enantiomer composition of the polylactide matrix. All five series of SS plates contained the same initial amount of the agent (loading of about 17%). While the series with highest content of L-lactide (series S, pure PLLA) exhibits the highest amount of drug released within the initial fast-release phase, with increasing content of D-lactide in the polymer composition (series R, S, T, with L-Lactide/D-Lactide ratio ranging from 0.9 to 0.7) the release profile gradually changes, showing lower fast-releasing fraction and better diffusion-controlled release. For compositions with about 30% of D-lactide units in the polymer, the release profile approaches that of series U, i.e., PDLLA (L-lactide/D-lactide=0.50). These data indicate, that for the ratios of L-LA/D-LA below 0.7 (i.e, for the content of D-lactide units in polylactide above 30%), the fraction of amorphous regions becomes dominant, and the exclusion of the drug from the crystalline regions does not significantly affect the distribution of the agent within the matrix. It is also worth noticing, that the release rates in the second (slow) phase of release are similar for all series, what is in accord with the prevalence of diffusion of agent molecules through the amorphous parts of the matrix, hence, that part of the matrix which has similar character in all five series.

The example demonstrates the mechanisms by which the ratio of crystalline and amorphous phases in polylactide blends and copolymers affects the release profile of the incorporated agent. It also demonstrates the range in the ratio of D/L enantiomers which is effective in modulation of the release rate through the ratio of crystalline/amorphous phases, indicating that compositions, either blends or copolymers, with L/D ratio below 0.7 (or, alternatively, above 0.3) behave as predominantly amorphous.

Example 13

Biological Effect of the Agent Released from the Polymer Coating

Series of SS plates (7.1×7.1 mm, surface area ~50 mm2) analogous to those described in Example 1, were activated by the reaction with APTES, grafted by polymerization of D,L-lactide by the procedure described in Example 1.1., and polymer-agent compositions consisting of either PDLLA or PLLA matrix with different loading of CVT313 were cast on one side of the SS plates. The plates were pre-incubated with PBS (phosphate buffered isotonic saline) for 17 hours to remove a fast releasing (burst) fraction of the incorporated drug, rinsed by the buffer and sterilized by exposure to UV light. A group of 3 plates was randomly selected from each series and used for determination of the release rate. The remaining plates in the series were used for tissue-culture experiments. Thus, series of plates V, W, X, and Y, releasing different daily doses of CVT313 into incubation medium in a constant, zero-order rate were prepared. The parameters of the series are displayed in Table 6. The release rate numbers given in Table 6 are doses delivered to each culture cell. The release rate numbers in parentheses are the numbers on a per cm2 basis.

TABLE 6

Characteristics of sustained-release coatings on the series of SS-plates

| Parameter/Series | V | W | X | Y |
|---|---|---|---|---|
| Number of plates in the experiment | 18 | 18 | 18 | 10 |
| Polymer matrix | PDLLA | PDLLA | PDLLA | PLLA |
| Container layer thickness (um) | 2.0 | 1.8 | 1.4 | 1.2 |
| CVT313 loading (% w/w) | 3.7 | 7.5 | 23 | 18 |
| Release rate (dose) (ng/day) | 27 (54) | 82 (164) | 222 (444) | 339 (678) |

The sterile plates were placed in the wells of a tissue-culture plate, which already contained pre-cultivated and well-adapted cells adhered to the bottom. 24-well culture plates were used with the cultivation surface of 2.0 cm$^2$/well, and the volume of the medium was 2.5 ml/well. 3T3 mouse fibroblasts were used as testing cell culture. 5000–10000 cells were seeded per well. At 24 hour intervals the culture medium was removed by aspiration and replaced by the same volume of the fresh one.

At given times, the designed plates, containing the treated wells with drug-loaded coupons, the wells with the control coupons and the control wells without any treatment were processed for MTT test. Triplicate wells were used for treated and control series for each time interval.

MTT test: The culture medium was removed and the MTT solution (3-(4,5-dimethylthiazol-2-yl)2,5-diphenyl tetrazolium bromide) in PBS (600 ul/well) was added to each well. The plates were incubated for 2 h in 37° C. The blue formazan stain formed was dissolved in iso-propanol and the optical density was measured using an automatic microplate reader. If needed, in cases of high contents of cells, the measured solution was appropriately diluted by iso-propanol for optical density readings. The relative cell proliferation, as a result of the inhibitory effect of the released drug, was determined as the ratio of the mean optical density of treated wells with respect to that of the controls.

The effect of sustained release of CVT-313 on the growth of 3T3 cells was expressed in terms of relative proliferation, i.e. as a ratio of quantity of cells grown under the influence of CVT-313 and that of the control (undisturbed culture). The values for the second control (the culture exposed to coupons coated with the polymer only, without the drug) are presented for a comparison. Table 7 shows the relative proliferation rates of mouse 3T3 fibroblasts exposed to CVT313 released from polymer coatings and to sham controls (SS plates coated by the polymer only, void of agent). n—not determined, because of complete inhibition of the cell growth.

TABLE 7

| Series | V | | W | | X | | Y | |
|---|---|---|---|---|---|---|---|---|
| Dose | 27 ng/day | | 82 ng/day | | 222 ng/day | | 339 ng/day | |
| released | CVT313 | control | CVT313 | control | CVT313 | control | CVT313 | control |
| day 3 | 1.00 | 1.03 | 0.88 | 1.03 | 0.42 | 0.98 | 0.30 | 0.98 |
| day 6 | 0.94 | 0.99 | 0.69 | 1.00 | 0.14 | 1.06 | 0.03 | 0.97 |
| day 9 | 0.93 | 1.04 | 0.64 | 1.04 | n | n | n | n |

The experiment shows that the CVT313, a CDK2 inhibitor, can be released from polymer coatings under this invention in a sustained release manner. The extend of inhibition effect can be controlled by the released dose, which in turn is dependent on the parameters of the coating as shown in this and previous examples.

Example 14

Stability of Stents Containing Biologically Active Agent

Series (n=10) of balloon expandable coronary stents (stainless steel, length: 16 mm, diameter in compressed state: 1.6 mm, Pulse Corporation) were surface activated by the reaction with APTES. Then the series was divided in two groups (n=5). Group A was grafted by the in situ polymerization of D,L-lactide using the procedure described in Example 1. Group B was left without grafting. Both groups of stents were coated by a composition consisting of poly (D,L-lactide), (PDLLA, Mw=625 000) and a biologically active agent, CVT313.

The coating of stents was accomplished by dipping the stent in a solution of PDLLA (44.0 mg) and CVT313 (3.57 mg) in dioxane (8.00 ml). The solvent was left to evaporate at room temperature and finally dried under vacuum. The average thickness of the coating layer was determined from the weight of coating and the surface area of the stents, taking the value of 1.22 g/cm3as the density of the coating layer. Average thickness thus determined was about 0.9 um. The average content of the active agent in the coating composition was 7.5% w/w.

The quality, uniformity and surface smoothness was examined by using a scanning electron microscope, SEM, (Jeol 200A). Both groups of stents exhibited a uniform, contiguous, and smooth coating layer on all surfaces of the stent struts.

Stents were than individually placed on the balloon of a balloon catheter for angioplasty and expanded to a diameter of 3.5–3.6 mm. The expanded stents were examined again by SEM. Observations of stents from group A (containing a grafted layer of the in situ polymerized D,L-lactide) and group B (without a grafted layer) were compared.

In some stents of the group B, the expansion of the stent produced cracks in the coating layer, which were typically located in the region of the highest stress due to stent deformation, such as inner surfaces of some strut loops.

On the other hand, all stents of group A (modified by polymerization grafting) exhibited a smooth and contiguous coating layer after the expansion. Neither cracks nor any signs of peeling the coating polymer layer were found.

This observation confirmed the beneficial effect of the binding polymer layer (obtained by grafting polymerization) on the stability of the coating layer and on its resistance to mechanical stress, that can be produce during use of some medical devices, such as coronary stents. The described experiment thus demonstrates the advantageous features of the coating procedure according to the invention.

Example 15

Surface Properties of the Polymer Coatings

Glass slides (20×20×0.18 mm) (n=20) were thoroughly washed by ethanol and water and dried under stream of air (Group A).

A group of slides A was separated (n=16) and their surfaces were activated by the reaction with the solution of 3(N,N-bis-hydroxyethylamino)propyl-triethoxysilane in acetone (1%).The glass slides were rinsed by acetone and dried in vacuum. (Group B)

A group of surface-activated glass slides of B was separated (n=12), they were placed in a reactor containing crystalline L-lactide (144 mg, 1.0 mmol) (Fluka GmbH, Switzerland). The reactor content was flushed with dry nitrogen in repeated nitrogen/vacuum cycles and dried under high vacuum. A solution of anhydrous toluene (20.0 ml) containing tin(II)-ethylhexanoate (Sn(II)-octoate, 4 mg (0.01 mmol)) was added under inert atmosphere to dissolve the lactide and cover the plates with solution. The solution was maintained at 80° C. for 64 hours to complete the grafting polymerization of lactide on the hydroxyethyl functional groups of the silane-activated glass surface. The slides were removed from the polymerization mixture, washed with hot toluene and methanol, and vacuum dried. (Group C)

A series of PLLA grafted glass slides (n=8) was selected from the group C. A PLLA layer was deposited on one side of each slide by spin casting a solution of PLLA (MW=365 000) in chloroform (0.8 mg/ml) and evaporating the solvent to dryness. The same procedure was applied to coat the other side of each slide. In this way we have prepared glass slides coated on both sides by a homogenous a uniform layer of PLLA. By means of a surface profiler (Tenkor, AlfaStep 400) the average thicknes of the coating PLLA layer was determined to be 124±8 nm. (Group D)

A series (n=4) of PLLA-coated glass slides of group D was selected and additionally coated by deposition of a skin layer on the top of PLLA-coating. The polymer used for deposition of the skin layer was a block copolymer poly(D, L-lactide-block-ethylene oxide) (PDLLA-b-MeO-PEO). The copolymer was obtained polymerization of D,L-lactide in toluene using (x-hydroxy, o-methoxy-poly(ethylene oxide) (MeO-PEO, MW=11000) as a macromolecular initiator with tin(II)-2-ethylhexanoate as a catalyst. The number average molecular weights of the PDLLA and MeO-PEO copolymer blocks were 17800 and 11000, respectively. The skin layer was deposited by spin casting a solution of PDLLA-b-MeO-PEO copolymer in acetone (0.5 mg/ml) on the PLLA-coated glass slides. Both sides of the slides were coated by the same procedure as for group D. (Group E).

Surface properties and interactivity of the polymer coatings in groups A through E were investigated by measurement of contact angles of polymer/water/air interfaces and by measurement of protein adsorption.

The dynamic contact angles, i.e advancing angle $\Theta_A$ and receding contact angle $\Theta_R$ of water on coated surfaces of glass slides were measured by Wilhelmi's plate Method using Krüiss tensiometer. The values of contact angles reflect the wettability of the surfaces and are indirectly proportional to the interfacial energy or hydrophilicity of the surface.

The values of contact angles (degrees) of the polymer-coating/water/air interfaces for the series surface coated glass slides.

| Series | $\Theta_A$ | $\Theta_R$ |
|---|---|---|
| A (clean glass) | 54.1 ± 1.2 | 40.9 ± 1.4 |
| B (silane activated) | 72.1 ± 3.4 | 59.7 ± 3.6 |
| C (PLLA grafted) | 82.1 ± 2.2 | 61.4 ± 2.4 |

-continued

| Series | $\Theta_A$ | $\Theta_R$ |
|---|---|---|
| D (PLLA deposited) | 81.5 ± 2.6 | 62.0 ± 2.8 |
| F (PDLLA-MeO-PEO) | 31.2 ± 1.6 | 32.4 ± 3.4 |

The values in the table demonstrate differences in surface energy (hydrophilicity) between the neat glass (series A) and glass slides with different types of polymer coating. The values of contact angles for PLLA-grafted and PLLA-deposited layers are practically identical, thus indicating that a confluent layer of the same polymer material, i.e. PLLA, was created by both covalent grafting and casting from solution. By applying a layer of the amphiphilic block copolymer PDLLA-b-MeO-PEO as solution in acetone, which does not dissolve PLLA sublayer, a hydrophilic skin was created as the outermost layer of the coating. The miscibility and, therefore, also good adhesion between the binding grafted polymer layer, the deposited PLLA layer simulating here a polymer container layer, and the polymer skin layer, was achieved by using polymers with compatible structures, i.e polylactide in all three sublayers. The hydropilicity of the skin layer is indicated by the lowest values of both advancing and receding contact angles.

The following additional observations have been made with the series D and E. While the PLLA layers cast on a neat glass or a glass just modified by the reaction with the silane reagent are unstable, i.e., they peel off the glass typically within one or two days of their incubation in the aqueous buffers, the PLLA layers of both series D and E, were stable and did not change contact angle values for more than 6 days of the duration of this experiment. This observation demonstrates the beneficial effect of covalently grafted binding polymer layer on the long-term applicability of the coating.

The adsorption of serum albumin on the surfaces of series C, D and E was followed by Comassie Blue staining, quantified by UV-VIS spectrophotometer (Pye-Unicam 6200). The adsorption of the protein on the glass slides with a hydrophilic skin coating made of PDLLA-b-MeO-PEO block copolymer was at a level of 15 to 20 percent of that for PLLA (series D and C). Thus, hydrophilic skin on a polylactide coating can provide for an antifouling properties of the surface and contribute to theimproved biocompatibility of the coated devices.

We claim:

1. A coating for a medical device having a body fluid-contacting surface for contacting blood or other body fluids, the coating comprising:
    a silane derivative covalently bonded to the surface of a medical device, said silane derivative containing hydroxyl or amino functional groups;
    a layer of lactone polymer chains grown on the hydroxyl or amino functional groups of the silane derivative through in-situ ring opening graft polymerization of lactone monomers, said polymerization initiated by the said hydroxyl or amino functional groups of the silane derivative covalently bonded to the surface of a medical device, said lactone polymer chains and said silane derivative together forming a grafted lactone polymer layer; and
    at least one polyester polymer/biologically active agent layer deposited on the grafted lactone polymer layer, wherein at least the first of the deposited polymer/biologically active agent layers is chemically compatible with the grafted lactone polymer layer to allow for entanglement of said deposited polyester polymer chains with the chains of said grafted lactone polymer chains for strong adhesion.

2. The coating of claim 1 wherein the at least one deposited polyester polymer layer comprises from about 0.5% to about 60% by weight of one or more biologically active agents.

3. The coating of claim 2 wherein the at least one deposited polyester polymer layer comprises from about 0.5% to about 34% by weight of one or more biologically active agents.

4. The coating of claim 2 wherein the biologically active agent is an anti-proliferative.

5. The coating of claim 4 wherein the biologically active agent is a CDK2 inhibitor.

6. The coating of claim 2 wherein the biologically active agent is an anti-inflammatory steroid.

7. The coating of claim 6 wherein the biologically active agent is dexamethasone.

8. The coating of claim 2 wherein the concentration of biologically active agent in the layers of the coating may be the same for each layer or the concentration may vary from layer to layer of the coating.

9. The coating of claim 1 wherein the grafted lactone polymer comprises poly(L-lactide) or poly(D,L-lactide).

10. The coating of claim 1 wherein the deposited polyester polymer layer is a polylactone homopolymer or a block copolymer comprising polylactone blocks.

11. The coating of claim 10 wherein the polyester component of the deposited polymer comprises a lactone homopolymer or a lactone copolymer, wherein the lactone homopolymer comprises polyglycolide, poly(L-lactide), poly(D-lactide), poly(ε-caprolactone), poly(p-dioxanone), poly(dioxepanone), or poly(D,L-lactide), or wherein the lactone copolymer comprises statistical or block copolymers, wherein the statistical or block copolymers comprise poly(L-lactide-co-D-lactide), poly(L-lactide-co-glycolide), poly(D-lactide-co-glycolide), poly(D,L-lactide-co-glycolide), poly(lactide-co-caprolactone), poly(lactide-co-dioxanone), or poly(lactide-co-dioxepanone).

12. The coating of claim 11 wherein the deposited polymer comprises poly(L-lactide) or poly(D,L-lactide).

13. The coating of claim 1 wherein the polyester polymer deposited on the grafted lactone polymer layer comprises two or more polyester polymer sublayers.

14. The coating of claim 13 wherein each of the deposited polymer sublayers is independently a lactone polymer, wherein the lactone polymer comprises lactone homopolymers or copolymers.

15. The coating of claim 14 wherein the lactone copolymer comprises a block copolymer wherein at least one polylactone block comprises polyglycolide, poly(L-lactide), poly(D-lactide), poly(ε-caprolactone), poly(p-dioxanone), poly(dioxepanone), poly(D,L-lactide), poly(L-lactide-co-D-lactide), poly(L-lactide-co-glycolide), poly(D-lactide-co-glycolide), poly(D,L-lactide-co-glycolide), poly(lactide-co-caprolactone), poly(lactide-co-dioxanone), or poly(lactide-co-dioxepanone) and, wherein the other block copolymer comprises polyalkyleneoxide, poly(amino acid), poly(acrylate), poly(methacrylate), or a polybutadiene.

16. The coating of claim 1 wherein the deposited polyester polymer has a molecular weight of $10^3$ to $10^6$.

17. The coating of claim 1 that further comprises a polymer skin or a topcoat layer deposited on the deposited polyester polymer layer.

18. The coating of claim 17 wherein the polymer skin or topcoat layer comprises a polyester polymer.

19. The coating of claim 18 wherein the polyester polymer is a lactone homopolymer or a lactone block copolymer, wherein the lactone homopolymer comprises polyglycolide, poly(L-lactide), poly(D-lactide), poly($\epsilon$-caprolactone), poly(p-dioxanone), poly(dioxepanone), or poly(D,L-lactide), or wherein the lactone copolymer comprises a statistical or block copolymer, wherein the statistical or block copolymer comprise poly(L-lactide-co-D-lactide), poly(L-lactide-co-glycolide), poly(D-lactide-co-glycolide), poly(D,L-lactide-co-glycolide), poly(lactide-co-caprolactone), poly(lactide-co-dioxanone), or poly(lactide-co-dioxepanone).

20. The coating of claim 1 wherein the medical device is a stent.

21. A coating for a medical device having a body fluid-contacting surface for contacting blood or other body fluids, the coating comprising:
a silane derivative layer covalently bonded to the body fluid-contacting surface of the medical device, said silane derivative layer containing hydroxyl or amino functional groups;
lactone polymer chains grown on the hydroxyl or amino functional groups of the silane derivative through in-situ ring opening graft polymerization of lactone monomers, said polymerization initiated by said hydroxyl or amino functional groups of the silane derivative covalently bonded to the surface of the medical device, said lactone polymer chains and said silane derivative together forming a grafted lactone polymer layer;
at least one polyester polymer/biologically active agent layer deposited on the grafted lactone polymer layer, wherein at least the first of the deposited polymer/biologically active agent layers is chemically compatible with the grafted lactone polymer layer to allow for entanglement of said deposited polyester polymer chains with the chains of said grafted lactone polymer chains for strong adhesion; and
optionally at least one polymer layer deposited on said deposited polyester polymer/biologically active agent layer forming a skin or topcoat layer.

22. A coating for a medical device having a body fluid-contacting surface for contacting blood or other body fluids, the coating comprising:
a silane derivative covalently bonded to the surface of a medical device, said silane derivative containing hydroxyl or amino functional groups;
a layer of lactone polymer grown on the hydroxyl or amino functional groups of the silane derivative through in-situ ring-opening graft polymerization of lactone monomers, said polymerization initiated by the said hydroxyl or amino functional groups of the silane derivative covalently bonded to the surface of a medical device, said lactone polymer chains and said silane derivative together forming a grafted lactone polymer layer, said grafted lactone polymer comprises a lactone homopolymer or a lactone copolymer, wherein the lactone homopolymer comprises polyglycolide, poly(L-lactide), poly(D-lactide), poly($\epsilon$-caprolactone), poly(p-dioxanone), poly(dioxepanone), or poly(D,L-lactide), or wherein the lactone copolymer comprises statistical or block copolymers, wherein the statistical or block copolymers comprise poly(L-lactide-co-D-lactide), poly(L-lactide-co-glycolide), poly(D-lactide-co-glycolide), poly(D,L-lactide-co-glycolide), poly(lactide-co-caprolactone), poly(lactide-co-dioxanone), or poly(lactide-co-dioxepanone); and
at least one polyester polymer/biologically active agent layer deposited on the bonded lactone polymer layer, wherein at least the first of the deposited polymer/biologically active agent layers is chemically compatible with the grafted lactone polymer layer to allow for entanglement of said deposited polyester polymer chain with the chains of said grafted lactone polymer chains for strong adhesion.

23. A coating for a medical device having a body fluid-contacting surface for contacting blood or other body fluids, the coating comprising:
a silane derivative covalently bonded to the surface of a medical device, said silane derivative containing hydroxyl or amino functional groups;
a layer of lactone polymer chains grown on the hydroxyl or amino functional groups of the silane derivative through in-situ ring-opening graft polymerization of lactone monomers, said polymerization initiated by the said hydroxyl or amino functional groups of the silane derivative covalently bonded to the surface of a medical device, said lactone polymer chains and said silane derivative together forming a grafted lactone polymer layer; and
two or more polyester polymer/biologically active agent layers deposited on the grafted lactone polymer layer, wherein at least the first of the deposited polymer/biologically active agent layers is chemically compatible with the grafted lactone polymer layer to allow for entanglement of said deposited polyester polymer chains with the chains of said grafted lactone polymer chains for strong adhesion.

24. A coating for a medical device having a body fluid-contacting surface for contacting blood or other body fluids, the coating comprising:
a silane derivative covalently bonded to the surface of a medical device, said silane derivative containing hydroxyl or amino functional groups;
a layer of lactone polymer chains grown on the hydroxyl or amino functional groups of the silane derivative through in-situ ring-opening graft polymerization of lactone monomers, said polymerization initiated by the said hydroxyl or amino functional groups of the silane derivative covalently bonded to the surface of a medical device, said lactone polymer chains and said silane derivative together forming a grafted lactone polymer layer;
two or more polyester polymer/biologically active agent layers deposited on the grafted lactone polymer layer, wherein at least the first of the deposited polymer/biologically active agent layers is chemically compatible with the grafted lactone polymer layer to allow for entanglement of said deposited polyester polymer chains with the chains of said grafted lactone polymer chains for strong adhesion; and
at least one polymer layer deposited on the topmost said deposited polyester polymer/biologically active agent layer forming a skin or topcoat layer.

25. The coating of claim 24 wherein at least one deposited polyester polymer layer comprises from about 0.5% to about 60% by weight of one or more biologically active agents.

26. The coating of claim 25 wherein the concentration of biologically active agent in the layers of the coating may be the same for each layer or the concentration may vary from layer to layer of the coating.

27. The coating of claim 25 wherein at least one deposited polyester polymer layer comprises from about 0.5% to about 34% by weight of one or more biologically active agents.

28. The coating of claim 25 wherein the biologically active agent is an anti-proliferative.

29. The coating of claim 28 wherein the biologically active agent is a CDK2 inhibitor.

30. The coating of claim 25 wherein the biologically active agent is an anti-inflammatory steroid.

31. The coating of claim 30 wherein the biologically active agent is dexamethasone.

32. The coating of claim 24 wherein the grafted lactone polymer comprises a lactone homopolymer or a lactone copolymer, wherein the lactone homopolymer comprises polyglycolide, poly(L-lactide), poly(D-lactide), poly(ε-caprolactone), poly(p-dioxanone), poly(dioxepanone), or poly(D,L-lactide), or wherein the lactone copolymer comprises statistical or block copolymers, wherein the statistical or block copolymers comprise poly(L-lactide-co-D-lactide), poly(L-lactide-co-glycolide), poly(D-lactide-co-glycolide), poly(D,L-lactide-co-glycolide), poly(lactide-co-caprolactone), poly(lactide-co-dioxanone), or poly(lactide-co-dioxepanone).

33. The coating of claim 32 wherein the grafted lactone polymer comprises poly(L-lactide) or poly(D,L-lactide).

34. The coating of claim 24 wherein at least the first deposited polyester polymer layer comprises at least one polyester polymer that is compatible or miscible with the grafted lactone polymer.

35. The coating of claim 34 wherein at least the first deposited polyester polymer layer is a polylactone homopolymer or a block copolymer comprising polylactone blocks.

36. The costing of claim 24 wherein the polyester component of at least one of the deposited polyester polymer/biologically active agent layers comprises a lactone homopolymer or a lactone copolymer, wherein the lactone homopolymer comprises polyglycolide, poly(L-lactide), poly(D-lactide), poly(ε-caprolactone), poly(p-dioxanone), poly(dioxepanone), or poly(D,L-lactide), or wherein the lactone copolymer comprises statistical or block copolymers, wherein the statistical or block copolymers comprise poly(L-lactide-co-D-lactide), poly(L-lactide-co-glycolide), poly(D-lactide-co-glycolide), poly(D,L-lactide-co-glycolide), poly(lactide-co-caprolactone), poly(lactide-co-dioxanone), or poly(lactide-co-dioxepanone).

37. The coating of claim 36 wherein the deposited polyester polymer comprises poly(L-lactide) or poly(D,L-lactide).

38. The coating of claim 24 wherein each of the deposited polyester polymer/biologically active agent sublayers is independently a lactone polymer, wherein the lactone polymer comprises lactone homopolymers or copolymers.

39. The coating of claim 38 wherein the lactone copolymer comprises a block copolymer wherein at least one polylactone block comprises polyglycolide, poly(L-lactide), poly(D-lactide), poly(ε-caprolactone), poly(p-dioxanone), poly(dioxepanone), poly(D,L-lactide), poly(L-lactide-co-D-lactide), poly(L-lactide-co-glycolide), poly(D-lactide-co-glycolide), poly(D,L-lactide-co-glycolide), poly(lactide-co-caprolactone), poly(lactide-co-dioxanone), or poly(lactide-co-dioxepanone) and, wherein the other block copolymer comprises polyalkyleneoxide, poly(amino acid), poly(acrylate), poly(methacrylate), or a polybutadiene.

40. The coating of claim 24 wherein the deposited polyester polymer has a molecular weight of $10^3$ to $10^6$.

41. The coating of claim 24 wherein the polymer layer deposited on the topmost said deposited polyester polymer/biologically active agent layer comprises a polyester polymer.

42. The coating of claim 41 wherein the polyester polymer deposited on the topmost said deposited polyester polymer/biologically active agent layer is a lactone homopolymer or a lactone block copolymer, wherein the lactone homopolymer comprises polyglycolide, poly(L-lactide), poly(D-lactide), poly(ε-caprolactone), poly(p-dioxanone), poly(dioxepanone), or poly(D,L-lactide), or wherein the lactone copolymer comprises a statistical or block copolymer, wherein the statistical or block copolymer comprise poly(L-lactide-co-D-lactide), poly(L-lactide-co-glycolide), poly(D-lactide-co-glycolide), poly(D,L-lactide-co-glycolide), poly(lactide-co-caprolactone), poly(lactide-co-dioxanone), or poly(lactide-co-dioxepanone).

43. The coating of claim 24 wherein the medical device is a stent.

44. A medical device having a coating over a body fluid-contacting surface of the medical device for contacting blood or other body fluids, wherein the coating comprises:
a silane derivative layer covalently bonded to the body fluid-contacting surface of the medical device, said silane derivative layer containing hydroxyl or amino functional groups;
lactone polymer chains grown on the hydroxyl or amino functional groups of the silane derivative through in-situ ring-opening graft polymerization of lactone monomers, said polymerization initiated by said hydroxyl or amino functional groups of the silane derivative covalently bonded to the surface of the medical device, said lactone polymer chains and said silane derivative together forming a grafted lactone polymer layer; and
at least one polyester polymer/biologically active agent layer deposited on the grafted lactone polymer layer, wherein at least the first of the deposited polymer/biologically active agent layers is chemically compatible with the grafted lactone polymer layer to allow for entanglement of said deposited polyester polymer chains with the chains of said grafted lactone polymer chains for strong adhesion.

45. The device of claim 44 wherein the coating comprises from about 0.5% to about 60% by weight of one or more biologically active agents.

46. The device of claim 45 wherein the coating comprises from about 0.5% to about 34% by weight of one or more biologically active agents.

47. The device of claim 45 wherein the biologically active agent is an anti-proliferative.

48. The device of claim 47 wherein the biologically active agent is a CDK2 inhibitor.

49. The device of claim 45 wherein the biologically active agent is an anti-inflammatory steroid.

50. The device of claim 49 wherein the biologically active agent is dexamethasone.

51. The device of claim 44 wherein the medical device is a stent.

* * * * *